(12) United States Patent
Miyazaki et al.

(10) Patent No.: US 8,303,275 B2
(45) Date of Patent: Nov. 6, 2012

(54) MICROPUMP, TUBE UNIT, AND CONTROL UNIT

(75) Inventors: Hajime Miyazaki, Matsumoto (JP); Kazuo Kawasumi, Chino (JP)

(73) Assignee: Seiko Epson Corporation (JP)

( * ) Notice: Subject to any disclaimer, the term of this patent is extended or adjusted under 35 U.S.C. 154(b) by 1122 days.

(21) Appl. No.: 11/951,371

(22) Filed: Dec. 6, 2007

(65) Prior Publication Data

US 2008/0138218 A1    Jun. 12, 2008

(30) Foreign Application Priority Data

Dec. 7, 2006    (JP) ................................. 2006-330156
Oct. 10, 2007    (JP) ................................. 2007-264206

(51) Int. Cl.
| F04B 43/08 | (2006.01) |
| F04B 43/12 | (2006.01) |
| F04B 45/06 | (2006.01) |
| F04B 45/08 | (2006.01) |

(52) U.S. Cl. .................................................. 417/477.1
(58) Field of Classification Search .................. 417/474, 417/476, 477.1, 477.2, 477.12, 477.3, 477.5, 417/477.7, 477.8, 477.6; 604/153
See application file for complete search history.

(56) References Cited

U.S. PATENT DOCUMENTS

| 3,574,883 A | 4/1971 | Brittain |
| 3,630,647 A * | 12/1971 | Kochlin ........................ 417/474 |
| 4,155,362 A | 5/1979 | Jess |
| 4,607,764 A | 8/1986 | Christine |
| 4,648,812 A | 3/1987 | Kobayashi et al. |
| 4,869,646 A | 9/1989 | Gordon et al. |
| 4,909,710 A | 3/1990 | Kaplan et al. |
| 4,954,046 A | 9/1990 | Irvin et al. |
| 5,049,047 A | 9/1991 | Polaschegg et al. |
| 5,318,413 A | 6/1994 | Bertoncini |
| 5,342,180 A | 8/1994 | Daoud |
| 5,531,697 A | 7/1996 | Olsen et al. |
| 5,531,698 A | 7/1996 | Olsen |
| 5,575,631 A | 11/1996 | Jester |

(Continued)

FOREIGN PATENT DOCUMENTS

JP    63-083477    6/1988

(Continued)

OTHER PUBLICATIONS

Communication from the European Patent Office dated Nov. 19, 2010, Application No. 09171345.3.

*Primary Examiner* — Devon Kramer
*Assistant Examiner* — Bryan Lettman
(74) *Attorney, Agent, or Firm* — Harness, Dickey & Pierce, P.L.C.

(57) ABSTRACT

A micropump of a peristaltic type that continuously transfers a fluid through depression of an elastic tube is disclosed. The micropump includes: a tube unit that includes the tube, a tube guide frame that fixedly holds the tube, a tube individual data storage section that stores tube individual data, and a depression mechanism section for depressing the tube; a control unit that is attachable to the tube unit, and includes a control circuit section that drives and controls a motor for driving the depression mechanism section, and a tube individual data processing section including a reader/writer unit that reads the tube individual data; and a power supply that makes an electrical supply to the control unit. In the micropump, the tube individual data is used as a basis for driving.

14 Claims, 13 Drawing Sheets

U.S. PATENT DOCUMENTS

| | | | |
|---|---|---|---|
| 5,647,854 A | 7/1997 | Olsen et al. | |
| 5,658,252 A | 8/1997 | Johnson | |
| 5,683,233 A | 11/1997 | Moubayed et al. | |
| 5,791,881 A | 8/1998 | Moubayed et al. | |
| 5,924,852 A | 7/1999 | Moubayed et al. | |
| 6,030,190 A | 2/2000 | Kammerer | |
| 6,106,249 A | 8/2000 | Barak | |
| 6,123,686 A | 9/2000 | Olsen et al. | |
| 6,164,921 A | 12/2000 | Moubayed et al. | |
| 6,253,968 B1 | 7/2001 | Van Dijk et al. | |
| 6,371,732 B1 | 4/2002 | Moubayed et al. | |
| 6,558,347 B1 | 5/2003 | Jhuboo et al. | |
| 6,749,587 B2 | 6/2004 | Flaherty | |
| 6,872,058 B2 | 3/2005 | Doig | |
| 7,036,751 B1 | 5/2006 | Lund et al. | |
| 7,059,840 B2 | 6/2006 | Corwin et al. | |
| 7,238,010 B2 | 7/2007 | Hershberger et al. | |
| 7,556,481 B2 | 7/2009 | Moubayed | |
| 7,632,079 B2 | 12/2009 | Hershberger et al. | |
| 7,762,795 B2 | 7/2010 | Moubayed | |
| 7,963,690 B2 | 6/2011 | Thompson et al. | |
| 8,152,498 B2 | 4/2012 | Bunoz | |
| 2004/0116862 A1 | 6/2004 | Ray | |
| 2004/0199118 A1* | 10/2004 | Christenson et al. | 604/151 |
| 2004/0234401 A1 | 11/2004 | Banister | |
| 2006/0029505 A1 | 2/2006 | Gibson et al. | |
| 2006/0073048 A1* | 4/2006 | Malackowski | 417/474 |
| 2006/0253086 A1 | 11/2006 | Moberg et al. | |
| 2007/0154336 A1 | 7/2007 | Miyazaki et al. | |
| 2007/0231205 A1 | 10/2007 | Williams et al. | |
| 2008/0051709 A1 | 2/2008 | Mounce et al. | |
| 2008/0065016 A1 | 3/2008 | Peterson et al. | |
| 2008/0101967 A1 | 5/2008 | Moubayed | |
| 2008/0101968 A1 | 5/2008 | Moubayed | |
| 2008/0138218 A1 | 6/2008 | Miyazaki et al. | |
| 2008/0138222 A1 | 6/2008 | Miyazaki et al. | |
| 2008/0304982 A1 | 12/2008 | Miyazaki et al. | |
| 2009/0060755 A1 | 3/2009 | Miyazaki | |
| 2009/0196776 A1 | 8/2009 | Moubayed | |
| 2009/0208350 A1 | 8/2009 | Miyazaki et al. | |
| 2009/0240201 A1 | 9/2009 | Rotem et al. | |
| 2009/0240210 A1 | 9/2009 | Walton et al. | |
| 2009/0312708 A1 | 12/2009 | Miyazaki et al. | |
| 2010/0021315 A1 | 1/2010 | Wolff | |
| 2010/0047099 A1 | 2/2010 | Miyazaki et al. | |
| 2010/0074781 A1 | 3/2010 | Miyazaki et al. | |
| 2010/0080720 A1 | 4/2010 | Miyazaki et al. | |
| 2010/0121306 A1 | 5/2010 | Yodfat et al. | |
| 2010/0143168 A1 | 6/2010 | Miyazaki et al. | |
| 2010/0296955 A1 | 11/2010 | Wolff | |
| 2011/0002801 A1 | 1/2011 | Miyazaki et al. | |
| 2011/0186143 A1 | 8/2011 | Miyazaki et al. | |
| 2011/0186598 A1 | 8/2011 | Thompson et al. | |
| 2011/0186599 A1 | 8/2011 | Thompson et al. | |
| 2011/0305588 A1 | 12/2011 | Miyazaki et al. | |
| 2012/0027624 A1 | 2/2012 | Miyazaki et al. | |

FOREIGN PATENT DOCUMENTS

| | | |
|---|---|---|
| JP | 3177742 | 11/1990 |
| JP | 06-021488 | 6/1994 |
| JP | 7-59853 | 3/1995 |
| JP | 2001-515557 | 9/2001 |
| JP | 2004-532670 | 10/2004 |
| JP | 2005-046632 | 2/2005 |
| JP | 2005-337212 | 12/2005 |
| JP | 2005-351131 | 12/2005 |
| JP | 2006-034845 | 2/2006 |
| JP | 2006-242116 | 9/2006 |
| JP | 2006-314346 | 11/2006 |
| JP | 2007-275548 | 10/2007 |
| JP | 2008-161669 | 7/2008 |
| JP | 2008-202602 | 9/2008 |
| JP | 2008-202603 | 9/2008 |
| WO | 97-34084 | 9/1997 |

* cited by examiner

MICROPUMP, TUBE UNIT, AND CONTROL UNIT

BACKGROUND

1. Technical Field

The present invention relates to a micropump of a peristaltic type that continuously transfers a fluid through depression of an elastic tube, and a tube unit and a control unit configuring the micropump.

2. Related Art

A previously known infusion pump infuses an infusion liquid filled in a liquid container, i.e., reserver, through depression of a tube. Such an infusion pump is configured to include tube depression means, drive means, and control means. The tube depression means continuously presses and closes a part of the tube, i.e., depression position, in such a manner as to make the infusion liquid to flow in accordance with the set quantity of the infusion liquid. The drive means includes a motor for driving the tube depression means, and the control means is for controlling the drive means. As an example, refer to Patent Document 1 (JP-A-7-59853, p. 3, and FIGS. 1 to 3).

With the infusion pump of Patent Document 1, an elastic tube linked to a reserver is attached, through insertion, to a peristaltic pump section of an infusion pump. An infusion liquid is managed in terms of quantity of flow through control over the rotation speed of the drive shaft of a motor. For control over the rotation speed as such, the pulse frequency in accordance with the set quantity of flow is supplied to a motor drive circuit.

The problem with such an infusion pump is that the tube varies in internal diameter, and this causes another variation of the quantity of infusion liquid. The variation of internal diameter is not negligible especially with infusion of a very small quantity.

Another problem with the infusion pump above is that when a user attaches a new tube to the infusion pump, there is no validation means to see whether the tube is made for attachment to the pump, thereby possibly causing wrong attachment of tube. When the liquid is drug preparations for medical treatment use, such wrong attachment is never permissible.

To prevent such a variation of internal diameter of the tube, and to prevent such wrong attachment of the tube, there is a possibility of fixing the combination between an infusion pump and a tube. This, however, requires replacement all at once of both the infusion pump and the tube being in a piece, and thus a problem of increasing the running cost is expected.

Another problem is that attaching the tube to the peristaltic pump section is difficult to be exact at position, and when the pump is smaller in size to allow a user to carry it around or to mount it to any other type of device, replacement and attachment of the tube may become difficult.

SUMMARY

An advantage of some aspects of the invention is to provide a micropump that implements the discharge of a fluid with high accuracy, prevents attachment of a tube not made for the micropump, and reduces the running cost.

A first aspect of the invention is directed to a micropump of a peristaltic type that continuously transfers a fluid through depression of an elastic tube. The micropump includes: a tube unit configured to at least include the tube, a tube guide frame that fixedly holds the tube, and a tube individual data storage section that stores therein tube individual data; a control unit that is attachable/detachable to/from the tube unit, and at least includes a control circuit section that drives and controls, via a transmission mechanism section, a motor for driving a depression mechanism section serving to depress the tube, and a tube individual data processing section that reads the tube individual data for data processing thereof; a power supply that makes an electrical supply to the control unit; and a reader/writer unit that detects attachment of the tube unit to the control unit, and reads the tube individual data for writing to the control unit. In the micropump, the tube individual data is used as a basis for driving.

In the first aspect of the invention above, the tube unit including the tube and the control unit can be both detachably attached to each other. Therefore, even if a fluid in a reserver runs out and requires replacement, there needs replacement only of the tube unit being less expensive than the control unit including the control circuit section, the tube individual data processing section, and others so that the running cost can be favorably reduced.

When a micropump is used for a long period of time, the tube may be changed in internal diameter or deteriorated by being repeatedly depressed by the depression mechanism section. This problem can be favorably solved by throwing away the tube unit including the tube, i.e., the tube unit is for one time use only, so that the tube can be replaced at low cost with another tube with a predetermined range of internal diameter and elasticity.

The tube is formed as a piece with the tube guide frame so that there are effects of easy replacement.

In the tube unit, the tube individual data storage section keeps, i.e., stores, therein tube individual data, and the reader/writer unit reads the tube individual data for writing into the control unit. Such tube individual data is used as a basis for driving and controlling the motor so that the resulting micropump achieves the quantity of fluid being highly accurate for transfer to each different tube.

Moreover, the reader/writer unit detects the attachment of the tube unit to the control unit, and to the control unit, writes any tube individual data of the tube to be driven. As such, any possible wrong attachment of a tube unit can be successfully prevented.

In the first aspect above, preferably, the tube individual data serves to correct a variation of a quantity of discharge of the fluid to be caused by a difference observed between the tube and another.

The expression of "a variation of a quantity of discharge of the fluid to be caused by a difference observed between the tube and another" is caused by, specifically, a variation of internal diameter of the tube, a variation of tube content of the peristaltic drive section, or others. In consideration thereof, the tube individual data is read by the control unit, and the tube individual data is used as a basis to drive and control the motor so that the resulting micropump achieves the quantity of fluid being highly accurate for transfer to each different tube.

In the first aspect above, preferably, the control unit further includes: a display section that at least displays thereon the tube individual data and a discharge program of the fluid; and an operation section that at least inputs the tube individual data and the discharge program of the fluid.

The discharge program includes the discharge speed of the fluid, the discharge time thereof, and others.

The display details on the display section include a value of tube individual data, setting details of a discharge program, the state of discharge, the warning message, and others.

With such a configuration, the resulting control unit including the control circuit, the display section, the operation section, and others is made more expensive than the tube unit. As such, replacing only the tube unit less expensive than the control unit will favorably lead to the reduction of the running cost.

In the first aspect above, preferably, the control unit further includes: a display section that at least displays thereon the tube individual data and a discharge program of the fluid; and an operation section for operating the control unit. In the micropump, the power supply is preferably provided to the control unit.

As described above, the tube individual data is input from the tube individual data storage section to the tube individual data processing section when the tube unit is attached to the control unit. Considering a possibility of an input failure from the tube individual data storage section to the tube individual data processing section, the operation section is made ready for such a data input so that the tube individual data becomes available as a basis to use the micropump.

In the first aspect above, preferably, the power supply is provided to the tube unit.

Herein, the power supply is not specifically restrictive, but may be a small-sized coin or button battery, for example.

When such a small-sized battery is used as a power supply, considering that the battery capacity thereof is small, the configuration of including the battery in the tube unit allows battery replacement at the time of replacement of the tube unit so that any possible problem such as battery exhaustion can be prevented during the use.

In the first aspect above, preferably, the control unit is configured to include the depression mechanism section, the transmission mechanism section, and the motor.

With such a configuration, the tube unit is configured to include the tube, the tube guide frame, and the tube individual data storage section, and the remaining movable components are housed in the control unit. As such, the tube unit is of simple configuration not including any movable component so that the running cost can be reduced to a further extent. There are other effects that attachment and detachment of the tube unit to/from the control unit becomes easier.

In the first aspect above, preferably, the tube unit is configured to include the depression mechanism section, and the control unit is configured to include the transmission mechanism section and the motor.

When the tube unit is configured to include the depression mechanism section for depressing the tube as such, any possible relative displacement can be suppressed between the tube and the depression mechanism section so that the accurate peristaltic movement to be transferred to the tube can be accurate.

In the first aspect above, preferably, the tube unit is configured to include the depression mechanism section, the transmission mechanism section, and the motor.

With such a configuration, the tube unit includes the drive components in its entirety, i.e., the drive components, i.e., the depression mechanism section, the transfer mechanism section, and the motor, are not separated from one another. This serves good when a user attaches or detaches the tube unit to/from the control unit, thereby eliminating any possible problem related to engagement among the drive components, and preventing any possible reduction of the assembly thereamong.

Although the details are left for later description, the motor for use with the micropump in the aspect of the invention is a stepper motor of the size of a watch for the purpose of size reduction and power saving. This thus allows to replace the motor at the same time as the replacement of the tube unit considering the heavy load driving of the motor so that the improvement of reliability can be achieved.

In the first aspect above, preferably, the depression mechanism section is a rotation cam that sequentially depresses a plurality of depression members with respect to the tube from an inflow side of the fluid to an outflow side thereof. The rotation cam is configured by a first cam that is fixed to a center shaft and a second cam that is pivotally supported by the center shaft, and the second cam is able to move from a position where the tube is free from the depression members to a position where the tube can be depressed thereby.

If the tube with elasticity is kept being depressed (pressed hard) for a long period of time at the same position by the depression members, the elasticity may be lost and the tube may be deformed. In consideration thereof, before the use of the micropump, the second cam is positioned at a position where the tube is free from the depression members, and after the start of driving, the second cam is moved to a position where the tube can be depressed by the depression members. This configuration favorably prevents deformation of the tube resulted from long-time depression (hard pressing) by the depression members at the same position of the tube.

In the first aspect above, preferably, the reader/writer unit is configured to include a transmission/reception control circuit section and a radio antenna that are provided to the tube individual data storage section for transmission of the tube individual data to the tube individual data processing section, and a transmission/reception data processing section and another radio antenna that are provided to the tube individual data processing section, and receive the tube individual data when the tube unit is attached to the control unit for data processing.

In the tube individual data storage section, the configuration of the transmission/reception control circuit section and the radio antenna is typified by an RFID (Radio Frequency Identification) tag (hereinafter, referred to as IC tag), for example. In the tube individual data processing section, the configuration of the transmission/reception data processing section and the radio antenna is typified by an RFID reader (hereinafter, simply referred to as reader), for example.

With such a configuration, an IC tag of the tube individual data storage section stores therein the tube individual data, and by radio communications means, the reader of the tube individual data processing section reads and writes the data so that the connection portion can be simplified in configuration between the tube unit and the control unit.

To the IC tag, the tube individual data can be input from the outside also by the radio communications means so that such an input of the tube individual data can be made after the tube unit is assembled.

The IC tag can be thin in thickness so that there are effects of being able to reduce the thickness of the tube unit.

In the first aspect above, preferably, the reader/writer unit is configured to include a storage circuit that is provided to the tube individual data storage section for storage of the tube individual data, and an input/output terminal provided to the tube individual data processing section, and establishes a connection to the storage circuit in response to attachment of, to the control unit, a reading circuit section that reads the tube individual data stored in the storage circuit, a data processing section that processes the tube individual data, and the tube unit.

In this configuration, the storage circuit is a nonvolatile memory, for example.

Such a configuration enables to acquire the tube individual data previously stored in the storage circuit into the control unit via the input/output terminal. As such, there are effects of being able to make inputs of the tube individual data without fail, and to simplify the configuration of the reading circuit section and that of the data processing section other than additionally providing the input/output terminal.

In the first aspect above, preferably, the reader/writer unit is configured to include a tube individual data display section that is provided to the tube individual data storage section for display of the tube individual data, and a reading/processing unit that is provided to the tube individual data for optical reading and data processing of the tube individual data when the tube unit is attached to the control unit.

In this configuration, the tube individual data display section is exemplified by a barcode, and the reading unit is exemplified by a barcode reader.

With a configuration in which the tube individual data display section being a barcode, the tube unit is attached only by a label printed with a barcode font. If this is the configuration, the tube individual data display section does not become thick that much. What is better, the barcode reader can be of general configuration.

A second aspect of the invention is directed to a tube unit that can be detachably attached to/from a control unit that drives and controls a micropump of a peristaltic type that continuously transfers a fluid through depression of an elastic tube. The tube unit includes: the tube; a tube guide frame that fixedly holds the tube; and a tube individual data storage section that stores therein tube individual data.

As an alternative configuration, the tube unit may be further provided with a depression mechanism section that depresses the tube, or may be further provided with a depression mechanism section that depresses the tube; a motor; and a transmission mechanism section that transfers the rotation of the motor to the depression mechanism section.

This configuration makes the tube unit available in isolation from the remaining components so that the cost reduction can be achieved for the micropump. The tube unit can be configured to include the above-described components in combination selected in accordance with the user's usage pattern.

A third aspect of the invention is directed to a control unit that can be detachably attached to/from a tube unit in a micropump of a peristaltic type that continuously transfers a fluid through depression of an elastic tube. The control unit includes: a display section that displays thereon tube individual data and a discharge program of the fluid; an operation section for use to operate the control unit; a control circuit section that drives and controls a motor; and a tube individual data processing section that reads tube individual data stored in the tube unit for data processing.

Alternatively, the control unit may be further provided with a transmission mechanism section that transfers the rotation of the motor to a depression mechanism section for depressing the motor and the tube, or provided with the depression mechanism section.

This configuration makes the control unit available in isolation from the remaining components so that the cost reduction can be achieved for the micropump. The control unit can be configured to include the above-described components in combination selected in accordance with the configuration of the tube unit described above and in accordance with the user's usage pattern.

BRIEF DESCRIPTION OF THE DRAWINGS

The invention will be described with reference to the accompanying drawings, wherein like numbers reference like elements.

DESCRIPTION OF EXEMPLARY EMBODIMENTS

In the below, embodiments of the invention are described by referring to the accompanying drawings.

Figure 7:
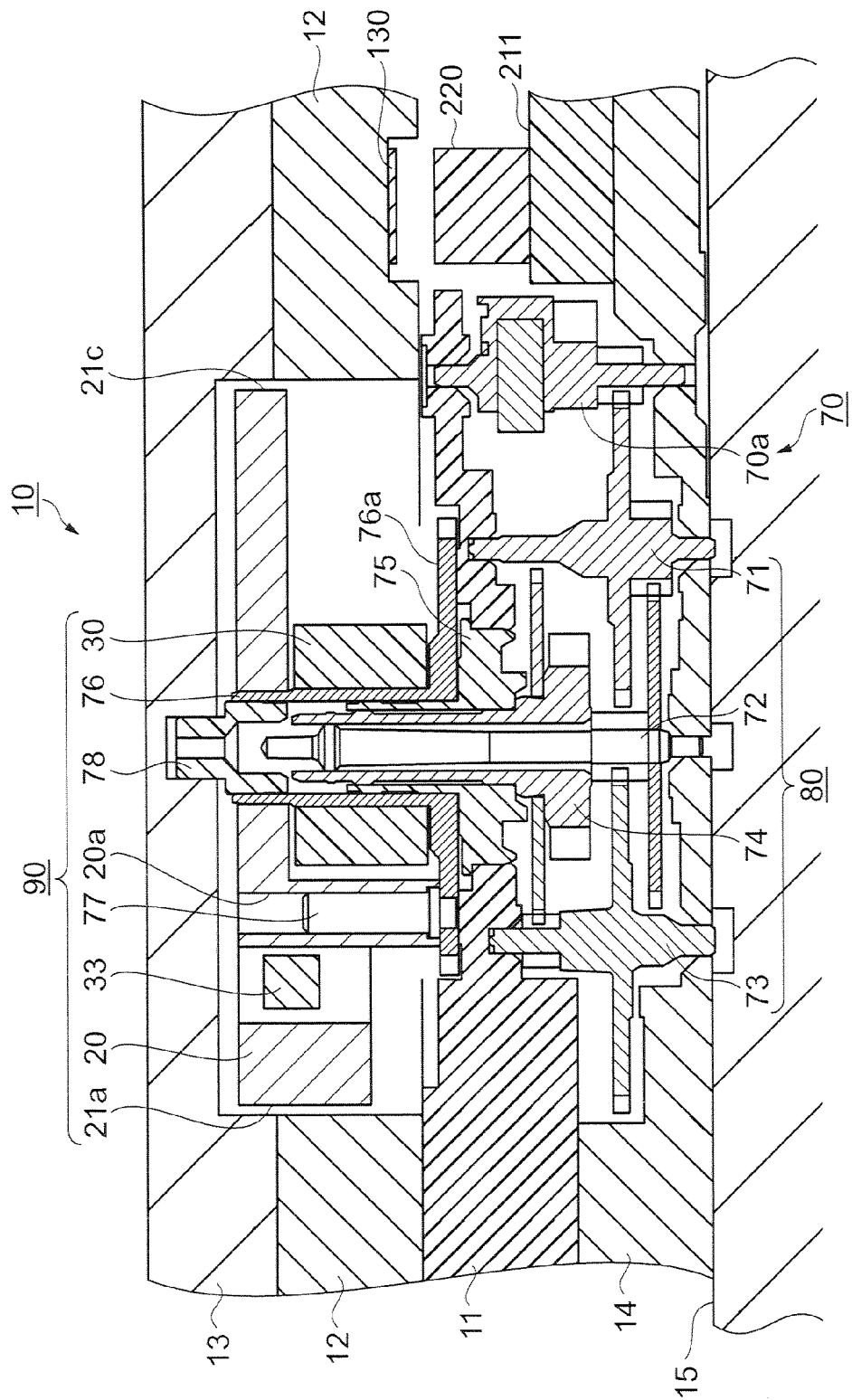
FIG. 7 is a partial cross sectional view of the micropump cut along a line B-B of FIG. 6.
Figure 8:
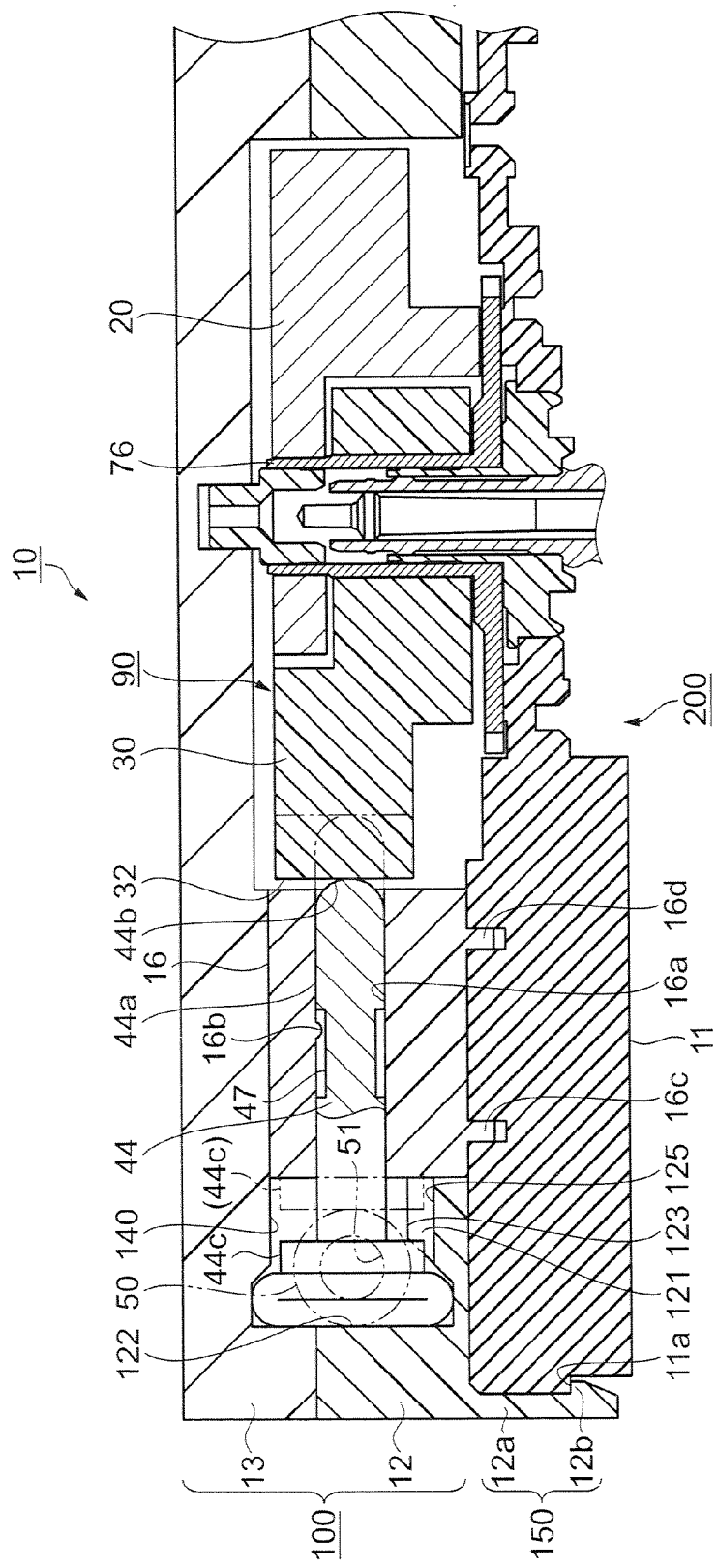
FIG. 8 is a partial cross sectional view of the micropump cut along a line C-C of FIG. 6.
Figure 9:
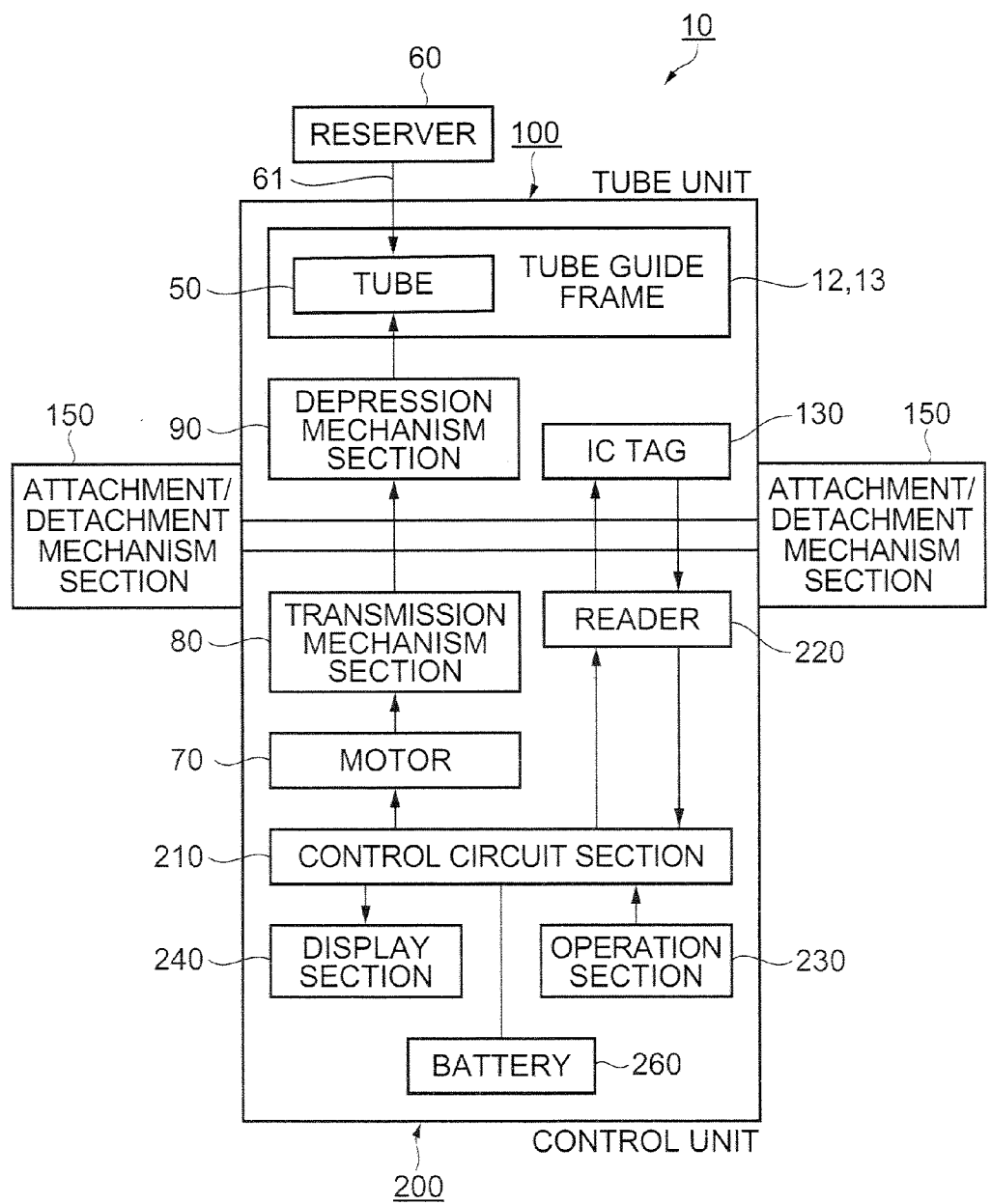
FIG. 9 is a diagram for illustrating the schematic configuration of a micropump in a second embodiment of the invention.
Figure 10:
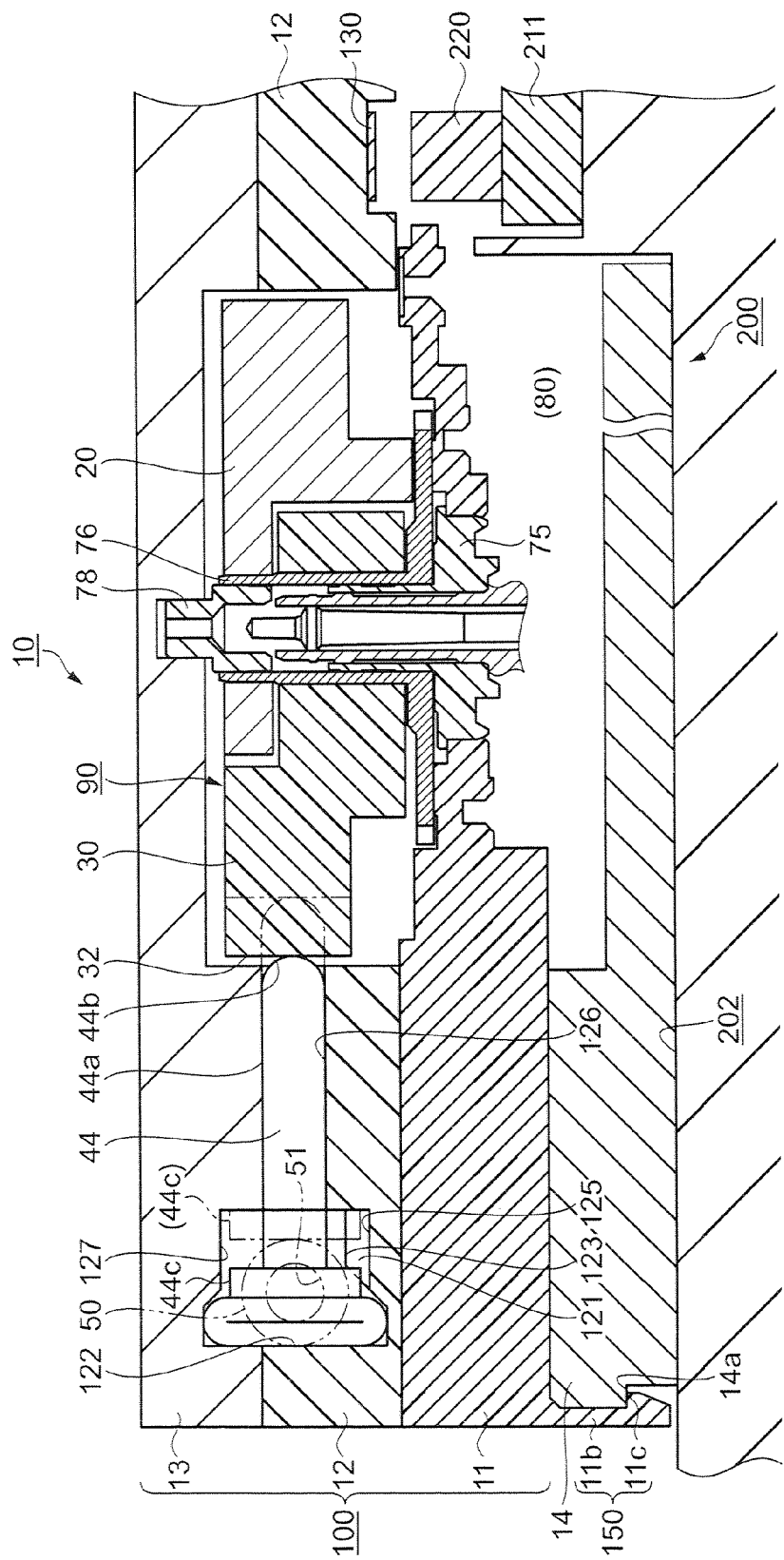
FIG. 10 is a partial cross sectional view of components, i.e., a tube unit, a depression mechanism section, and an attachment/detachment mechanism section, in the second embodiment of the invention.
Figure 11:
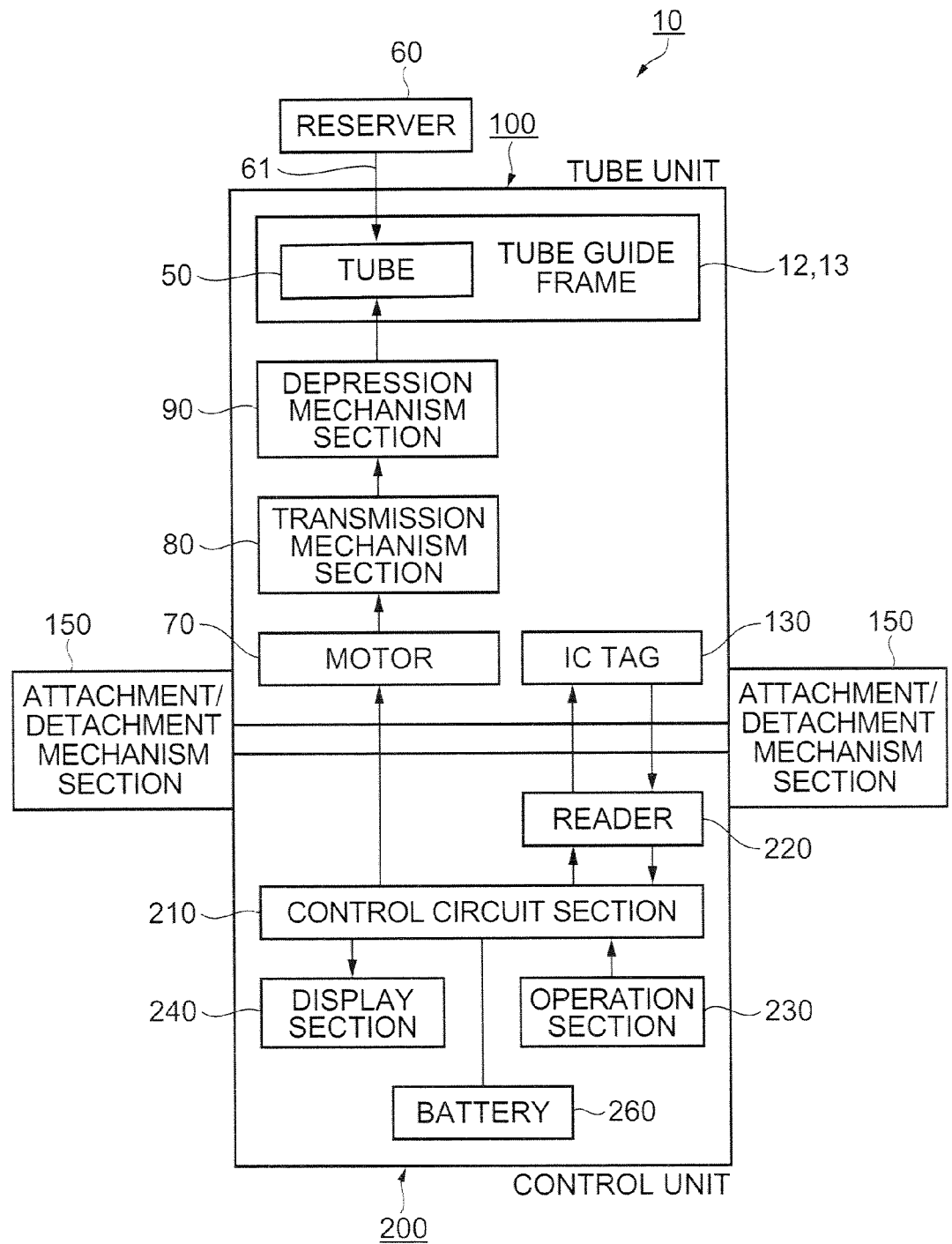
FIG. 11 is a diagram for illustrating the schematic configuration of a micropump in a third embodiment of the invention.
Figure 12:
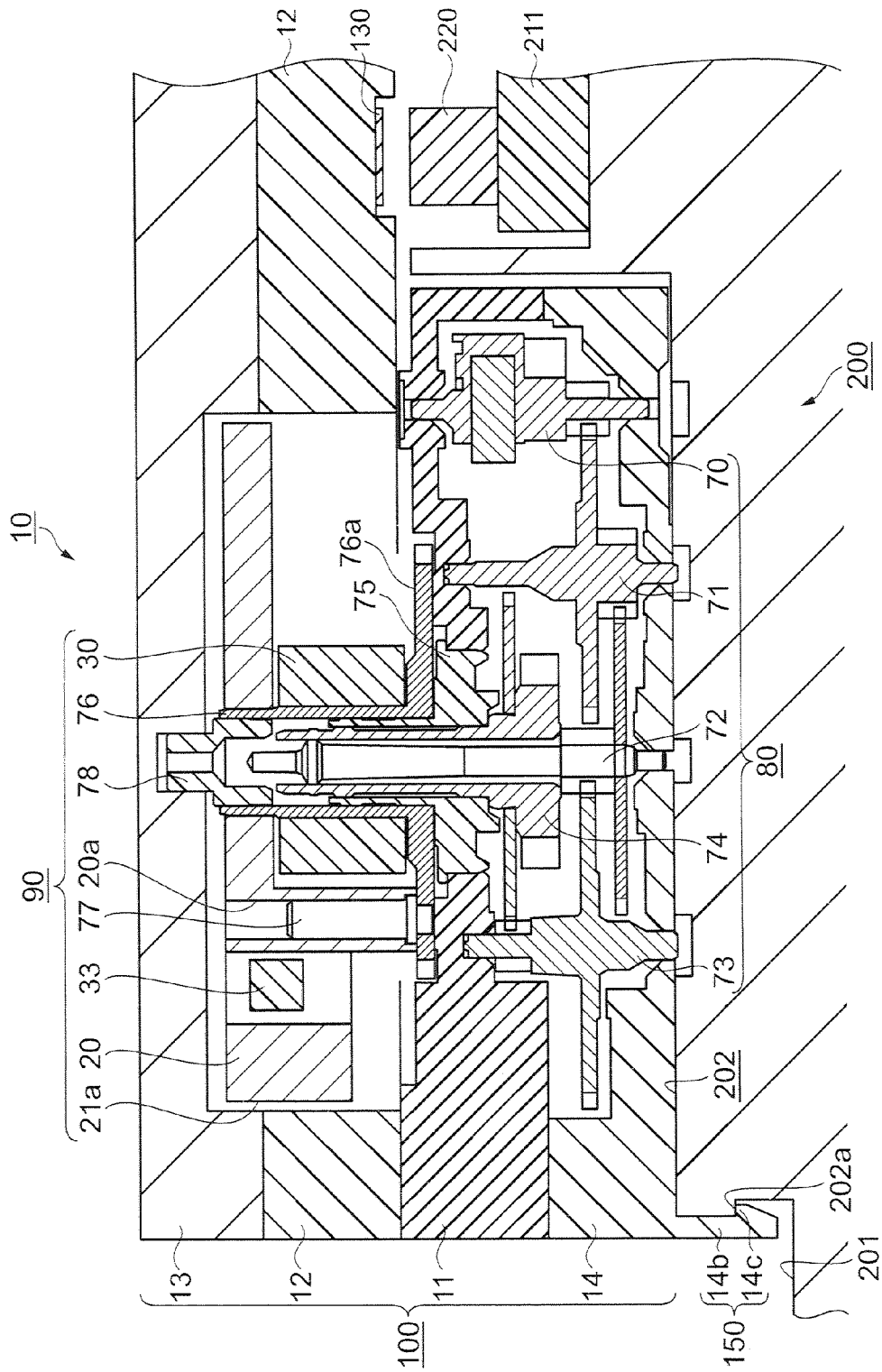
FIG. 12 is a partial cross sectional view of a tube unit and a control unit in the third embodiment of the invention, showing the relationship therebetween.
Figure 13:
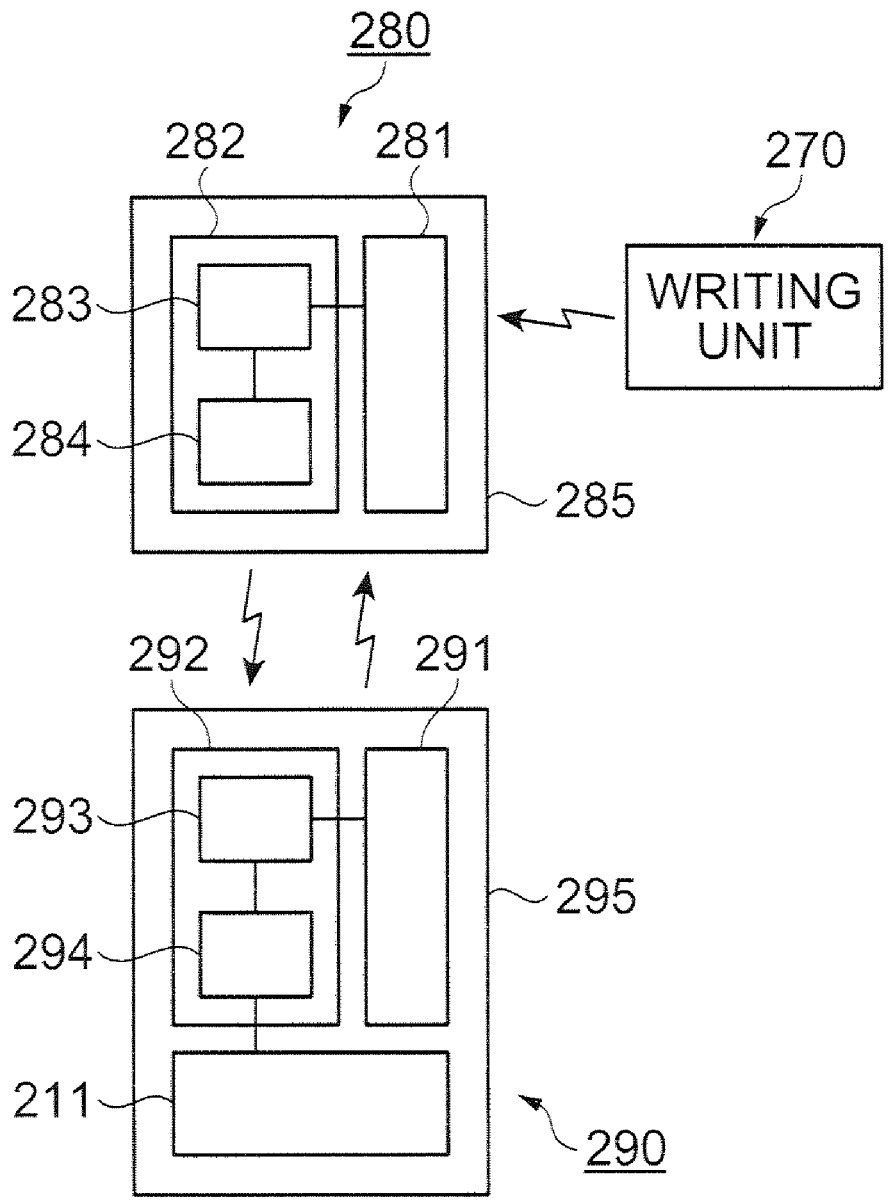
FIG. 13 is a diagram showing the schematic configuration of a tube individual data storage section and that of a tube individual data processing section in a fourth embodiment of the invention.
Figure 14:
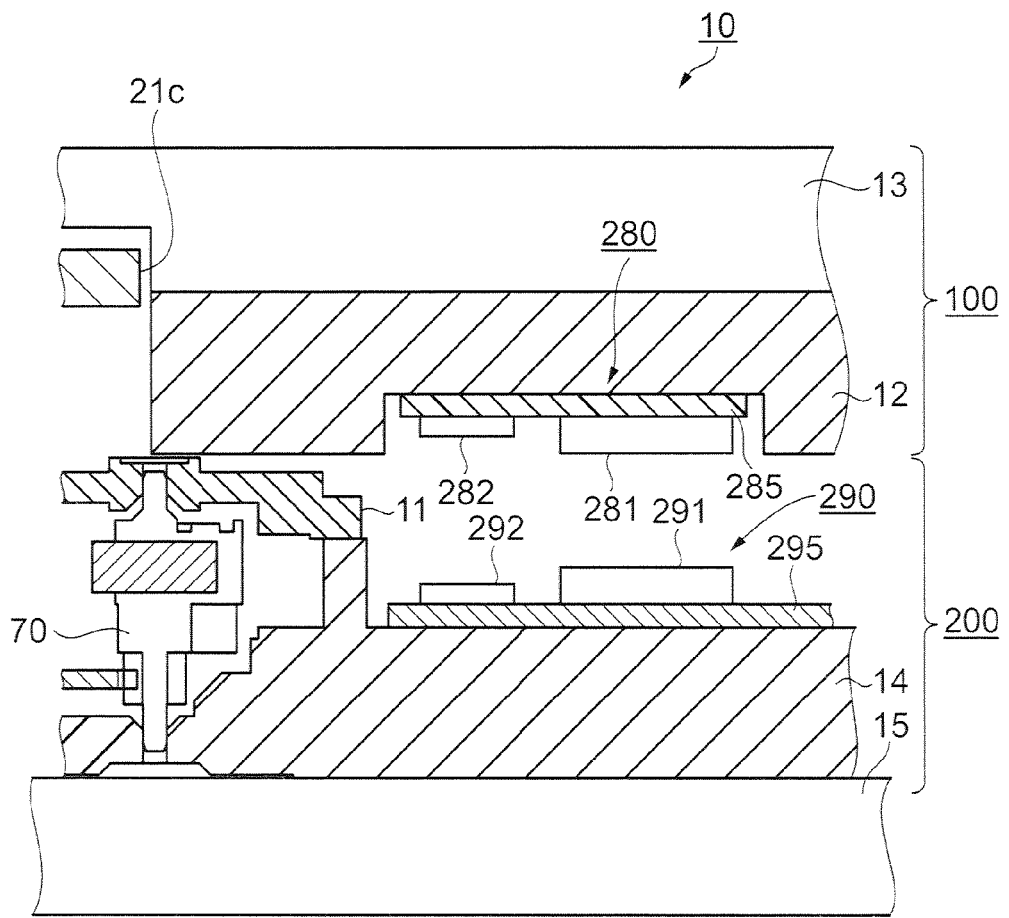
FIG. 14 is a partial cross sectional view of the tube individual data storage section and that of the tube individual data processing section in the fourth embodiment of the invention, showing the schematic configuration thereof.
Figure 15:
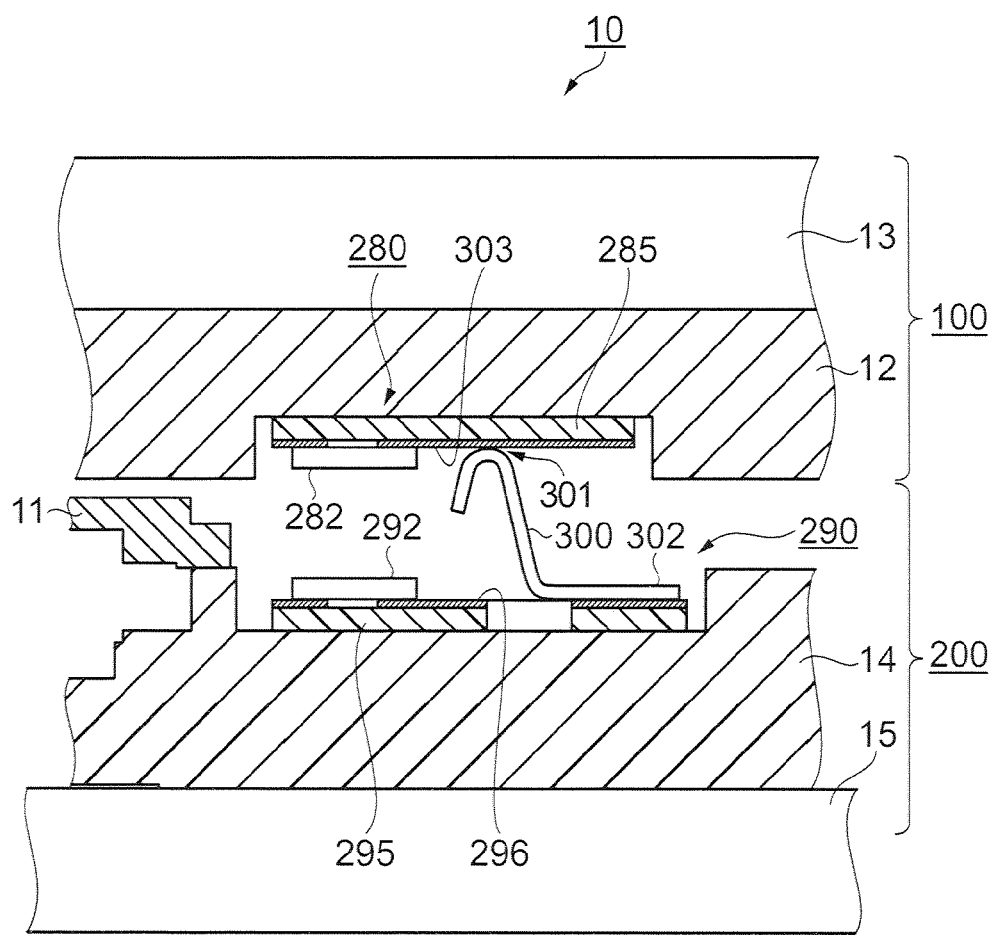
FIG. 15 is a partial cross sectional view of a tube individual data storage section and that of a tube individual data processing section in a fifth embodiment of the invention, showing the schematic configuration thereof.

FIGS. 1 to 8 each show a micropump of a first embodiment, and FIGS. 9 and 10 are for a second embodiment, FIGS. 11 and 12 are for a third embodiment, FIGS. 13 and 14 are for a fourth embodiment, and FIG. 15 is for a fifth embodiment.

The drawings to be referred to in the below are schematic drawings in which members and an aspect ratio are different from those in real world for the sake of convenience.

First Embodiment

Figure 1:
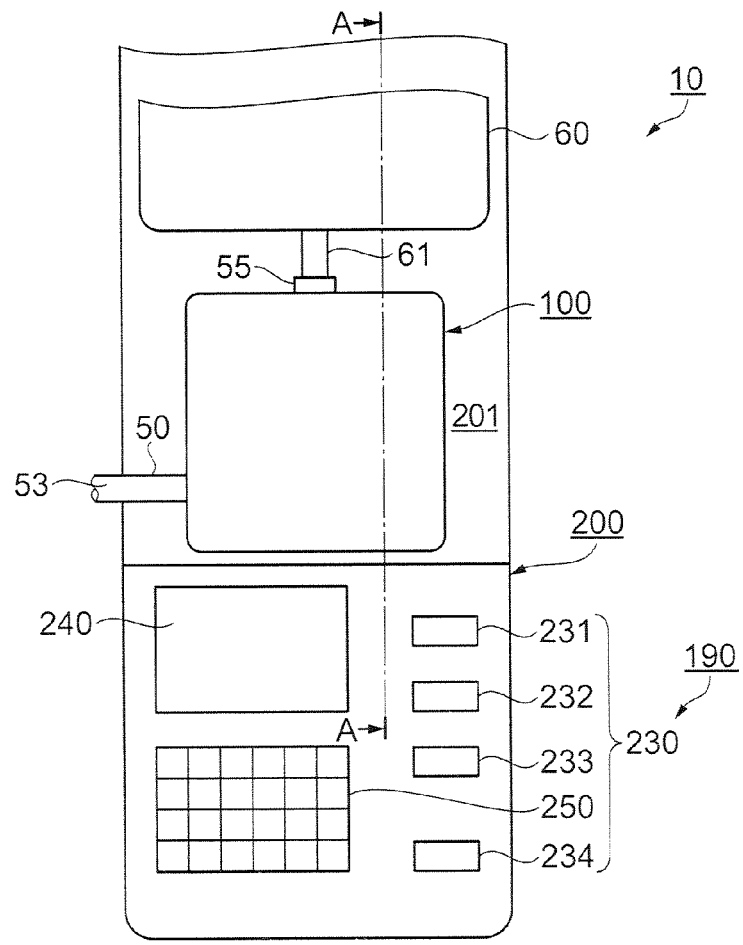
FIG. 1 is a plan view of a micropump in a first embodiment of the invention, showing the schematic configuration thereof.
Figure 2:
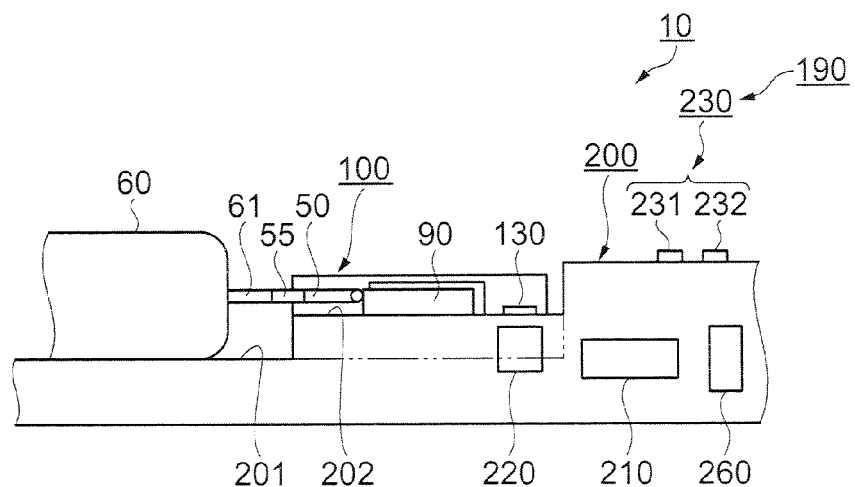
FIG. 2 is a cross sectional view of the micropump cut along a line A-A of FIG. 1.

FIG. 1 is a plan view of a micropump in a first embodiment of the invention, showing the schematic configuration thereof, and FIG. 2 is a cross sectional view of the micropump cut along a line A-A of FIG. 1. In FIGS. 1 and 2, a micropump 10 is configured to include a control unit 200, and a tube unit 100 that is detachably attached to the control unit 200. The tube unit 100 is linked with a reserver 60 via a connection tube 61. The reserver 60 houses therein a fluid, which is described as a liquid in the below.

The control unit 200 is provided with, on the surface side, a display/operation section 190 and a base 201 for placement thereon of the reserver 60. A part of the base 201 is protruding like a shelf in the thickness direction, and the protruding portion, i.e., a shelf-like section 202, serves as the interface section for the tube unit 100 and the control unit 200. The tube unit 100 is attached to the shelf-like section 202.

In the tube unit 100, an elastic tube 50 is attached to a portion between fourth and third frames 12 and 13 (refer to FIG. 8) each serving as a tube guide frame. The tube 50 is partially compressed by the peristaltic movement of a depression mechanism section 90 provided to the control unit 200.

The tube 50 is attached, at one end, with a connection tube 55, which is connected with the connection tube 61 linked to the reserver 60. The other end of the tube 50 is protruding from the tube unit 100 to the outside, and the tip end portion thereof is an outflow port 53 for the liquid.

A reader/writer unit is configured to include an IC tag 130 and a reader 220. The IC tag 130 is provided to the tube unit 100, and the reader 220 is provided to the control unit 200. The IC tag 130 is affixed to the lower surface side of the tube unit 100, i.e., on the side of the shelf-like section 202. At the position opposing this IC tag 130, the reader 220 equipped with a transmission/reception data processing section and a radio antenna is provided to the control unit 200.

The control unit 200 is provided with a display section 240 and the display/operation section 190 on the plane surface at a position of not intersecting the reserver 60 and the tube unit 100. Although not shown, the display section 240 makes various displays thereon by alphanumeric characters, e.g., values of tube individual data, setting details of a discharge program (e.g., a plurality of discharge speed values and discharge time values), state of discharge (e.g., display of discharge or no discharge, current discharge speed, lapse of time for discharge, and accumulated quantity of discharge), and warning messages (e.g., when a power supply is of a driving voltage or lower, and when there is no liquid supply from the reserver 60).

Among these various displays, the warning display is always displayed, and the remaining displays are selectively made through mode switching made through the operation of an operation section 230. As an alternative configuration, the display section 240 may be divided into a plurality of display portions for display of each different display details.

The operation section 230 is configured to include an ON/OFF switch 231, a display mode button 232, a tube individual data acquisition button 233, a discharge start/stop button 234, and a setting operation section 250. The ON/OFF switch 231 serves to turn ON and OFF the power supply of the control unit 200, and the display mode button 232 serves to change the display details of the display section 240. The discharge start/stop button 234 serves to start or stop the discharge of a liquid, and the setting operation section 250 serves to set a discharge program. Note here that the setting operation section 250 is of a keyboard configuration. In addition to these operation buttons, a clear button may be provided for use to rest the display details.

Alternatively, the operation section 230 may be so configured that the operation of the setting operation section 250 enables direct inputs of tube individual data to a control circuit section 210.

The control unit 200 carries therein the reader 220 described above, the control circuit section 210 that controls over the entire system of the control unit 200, and a battery 260 being a power supply.

Described next are the configurations and effects of the components in the micropump 10 described above.

Figure 3:
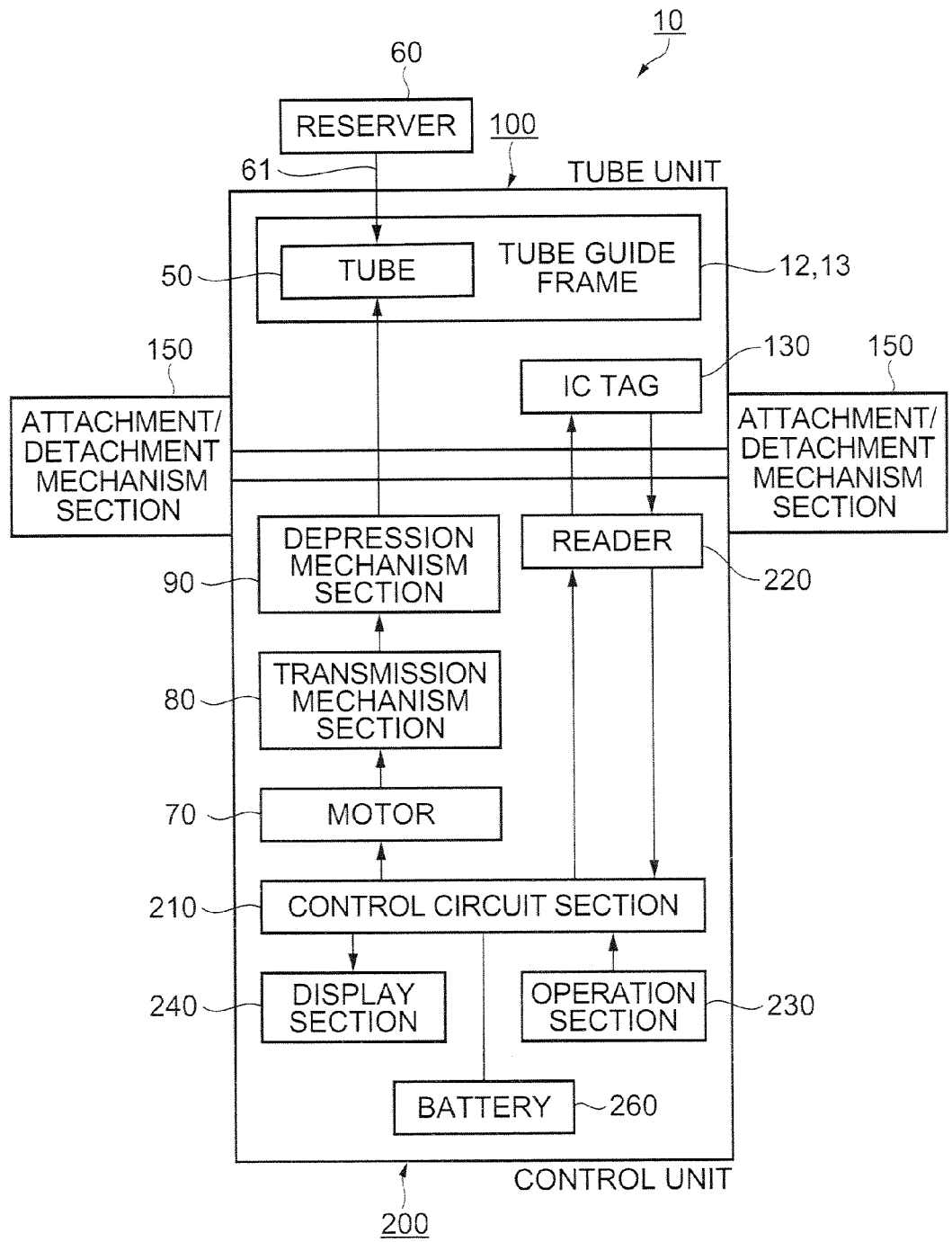
FIG. 3 is a diagram for illustrating the schematic configuration of the micropump in the first embodiment of the invention.

FIG. 3 is a diagram for illustrating the schematic configuration of the micropump of the first embodiment. In FIG. 3, the micropump 10 is configured by two units, i.e., the tube unit 100 and the control unit 200. These units are both driven while being detachably attached to each other by an attachment/detachment mechanism section 150, and discharge a liquid therefrom.

The tube unit 100 is configured to include the tube 50, the fourth and third frames 12 and 13 (referred also to FIG. 8) each being a tube guide frame, and the IC tag 130. The tube unit 100 is linked to the reserver 60 by the connection tube 61. The reserver 60 is a container for housing therein a liquid such as water, salt water, liquid preparations, oil, aromatic liquid, and ink, or a gas, for example.

The IC tag 130 stores therein tube individual data for use to correct any variation observed in the quantity of discharge of a fluid. Such a variation is caused due to a difference among tubes to be attached, e.g., the inner diameter of the tube 50 to be attached, or the quantity of the tube contents of the peristaltic section. As such, in this embodiment, the IC tag 130 is the tube individual data storage section.

The tube individual data also includes a correction value with respect to a reference value of the inner diameter of the tube 50 or that of the quantity of the tube contents of the peristaltic section, and a correction value with respect to a reference value of the actual measurement value of the tube 50 in terms of discharge.

The inner diameter of the tube 50 varies in manufacturing, and predictably, the resulting difference from the design inner diameter, i.e., reference value, causes a difference of the quantity of discharge of a liquid.

In consideration thereof, the inner diameter is input to the control unit for every tube in use, and a difference of the input value from the reference value is used as a basis to set the driving conditions to derive a predetermined value for the quantity of discharge.

The correction value R is denoted by $R=(d/D)^2$ where D denotes the diameter of a design value, i.e., reference value, of the fluid flowing section, i.e., inner diameter, of the tube, and d denotes the actual measurement value of the diameter of the tube 50 to be driven. With an input of this correction value, the driving conditions are accordingly set. The quantity of tube contents of the peristaltic section is handled similarly to the inner diameter of the tube.

Herein, because the tube 50 is formed by a material being elastic, a very slight amount of vaporization to the outside may be observed when a liquid flows inside. As such, another correction value is provided for the possible amount of vaporization from the tube 50. The correction value for the amount of vaporization is calculated from the ratio between the design liquid flow and the actual measurement value of the amount of vaporization.

The tube individual data also includes identification data of the tube unit 100, i.e., identification code. The identification code is set for every tube unit.

The control unit 200 is configured to include the depression mechanism section 90, a motor 70, and a transfer mechanism section 80. The depression mechanism section 90 serves as a drive mechanism of the micropump 10, and the transfer mechanism section 80 transfers the rotation of the motor 70 to the depression mechanism section 90. The tube individual data processing section is configured to include the reader 220, the control circuit section 210, the display section 240, the operation section 230, and the battery 260. The reader 220 serves as a transmission/reception data processing section to receive the tube individual data from the IC tag 130 for data processing, and the control circuit section 210 serves to control the micropump 10 in its entirety.

As to the micropump 10, the configuration and the driving effects of the drive mechanism are described later by referring to FIGS. 6 to 8.

Although not shown, the control circuit section 210 is configured to include a motor control circuit, a processing circuit, a driver, a timer, an operation control circuit, a power supply circuit, and others. The motor control circuit serves to drive and control the motor 70, and the processing circuit computes the discharge speed, the quantity of discharge, and others per unit time based on incoming tube individual data. The driver serves to drive the display section 240, and the timer serves to control the discharge time. The operation control circuit serves to process an incoming signal from the operation section 230, and the power supply circuit serves to control and monitor the battery voltage.

Described next is the configurations and effects of the IC tag 130 and the reader 220 by referring to the drawings.

Figure 4:
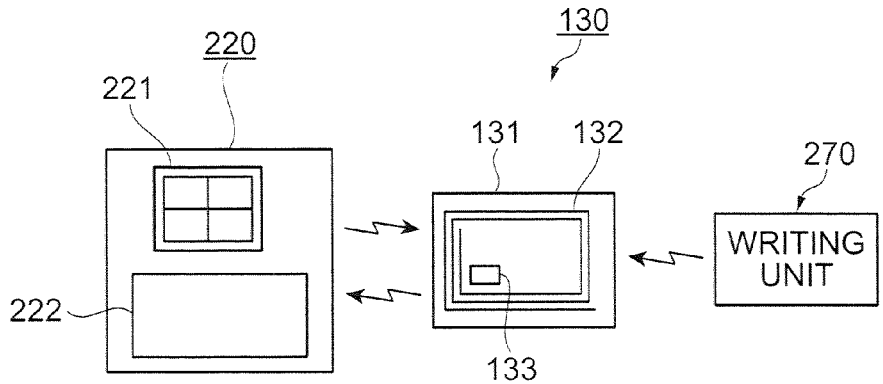
FIG. 4 is a diagram showing the configuration of an IC tag and that of a reader in the first embodiment of the invention.
Figure 5:
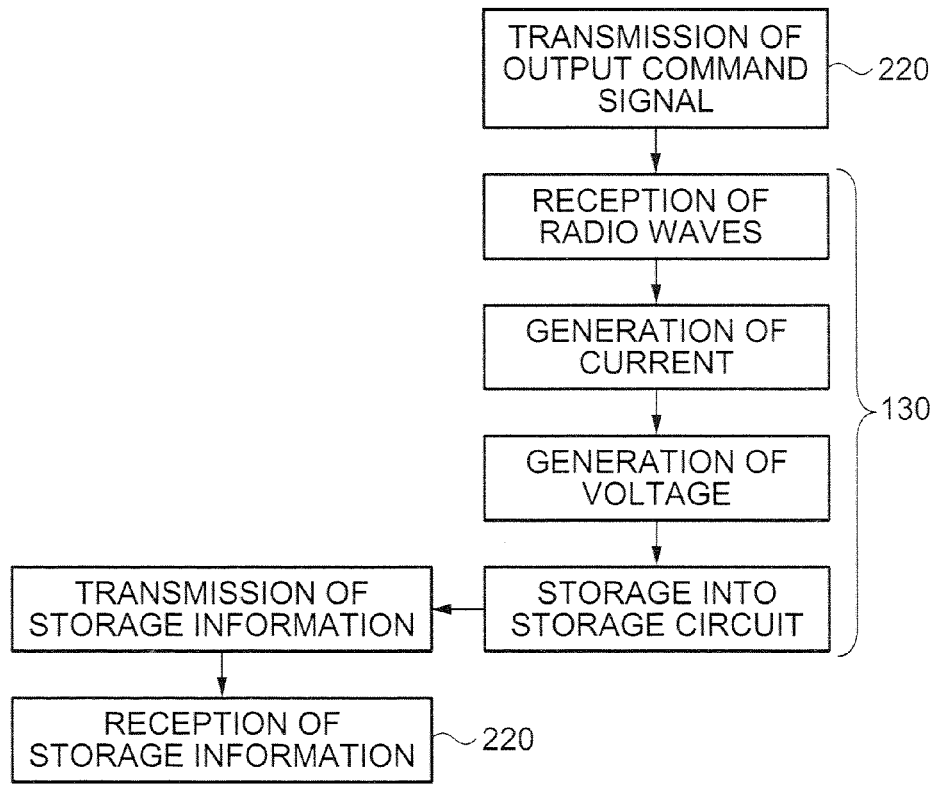
FIG. 5 is a diagram showing the effects of the IC tag and those of the reader in the first embodiment of the invention.

FIG. 4 is a diagram showing the configuration of the IC tag and that of the reader, and FIG. 5 is a diagram showing the effects thereof. In FIG. 4, the IC tag 130 is configured to include an IC chip 133 and a radio antenna 132. The IC chip 133 is provided on the surface of a substrate 131 for use as a transmission/reception control circuit section, and the radio antenna 132 is formed around the IC chip 133 disposed on the surface of the substrate 131 as such. The IC chip 133 includes a storage circuit (not shown), and stores therein the tube individual data. The tube individual data is input by a writing unit 270 through radio communications, and is stored in the storage circuit. Alternatively, the data may be stored in advance in the storage circuit.

The reader 220 is configured to include a planar antenna 221 and a transmission/reception data processing circuit 222 serving as a transmission/reception data processing section.

The attachment of the tube unit 100 and the control unit 200 is detected by communications between the IC tag 130 and the reader 220. The tube individual data stored in the IC chip 133, i.e., storage circuit, is read by the reader 220 through proximity radio communications. For data reading as such, the tube unit 100 and the control unit 200 are each provided with a connection terminal (not shown), and the attachment of the tube unit 100 and the control unit 200 are detected by these connection terminals. In response, an output command signal is issued from the reader 220, and the tube individual data is transmitted from the IC tag 130.

Alternatively, in the state that the tube unit 100 is attached to the control unit 200, the tube individual data acquisition button 233 (refer to FIG. 1) may be operated, and an output command signal may be forwarded to the IC tag 130. The tube individual data acquisition button 233 is the one provided to the control unit 200. In response to such an input of the output signal, the tube individual data may be transmitted from the IC tag 130 to the reader 220.

In FIG. 5, when the IC tag 130 receives the output command signal from the reader 220 as radio waves, generation of current and voltage occurs to the radio antenna 132. The IC tag 130 then converts the tube individual data, i.e., storage information, stored in the storage circuit into radio waves, and forwards the resulting radio waves to the reader 220.

Described next is the operation of the micropump by referring to FIGS. 1 to 3. The control circuit section 210 uses the tube individual data as a basis to compute the discharge speed, the quantity of discharge, and others per unit time, and displays the computation result on the display section 240. The setting operation section 250 is then operated so that the speed and time of discharge are set. In the control circuit section 210, the above-described speed of discharge per unit time is used as a basis to set the driving speed for the motor 70.

Thereafter, when the micropump 10 is driven through operation of the discharge start/stop button 234, the motor 70 is accordingly driven at the set driving speed. The driving speed is then reduced or increased in the transfer mechanism section 80, and the depression mechanism section 90 is driven by the resulting speed. The peristaltic movement of the depression mechanism section 90 discharges the liquid housed inside of the reserver 60 from the outflow port 53.

Described next is the drive section of the embodiment by referring to the drawings.

Figure 6:
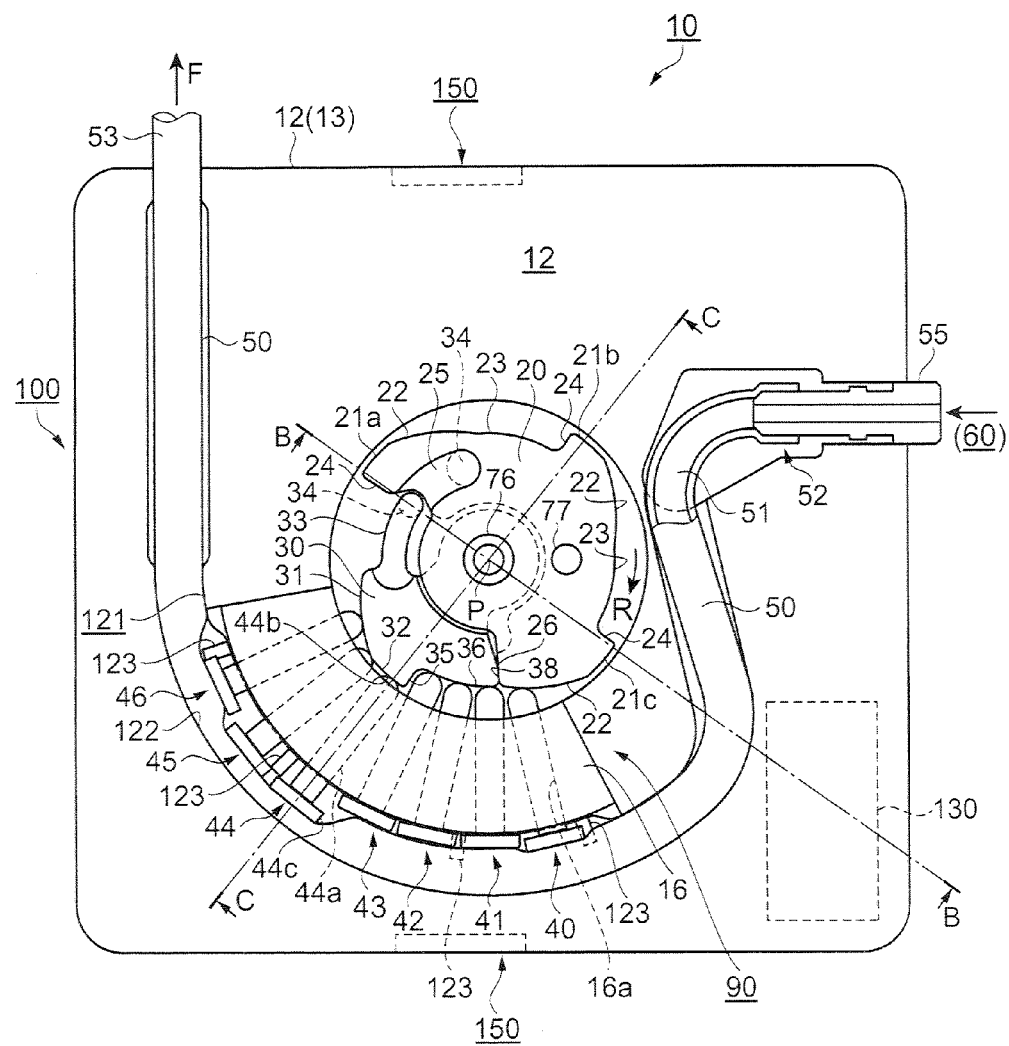
FIG. 6 is a plan view of a part of the micropump in the first embodiment of the invention.

FIG. 6 is a plan view of a part of the micropump in the embodiment, FIG. 7 is a partial cross sectional view of the micropump cut along a line B-B of FIG. 6, and FIG. 8 is a partial cross sectional view of the micropump cut along a line C-C of FIG. 6.

By referring to FIGS. 6 to 8, described next is the configuration of the micropump in this embodiment. In FIGS. 6 to 8, the micropump 10 is configured to include the transmission mechanism section 80 that transmits the driving force to the depression mechanism section 90, and the tube 50 through which a liquid flows. The micropump 10 is of a peristaltic type that depresses a depression member through rotation of a rotation cam, thereby making a fluid flow while sequentially closing the tube 50 from the inflow side of the fluid to the outflow side thereof. The rotation cam is configured by first and second cams 20 and 30, and is rotated by the driving force coming from the transmission mechanism section 80.

Described first is the configuration of the transmission mechanism 80 by referring to FIG. 7. In FIG. 7, the transmission mechanism section 80 is equipped with a stepping motor for use in a watch as the motor 70, and transmits the rotation of a coil and a stator (both not shown) and a step rotor 70a to a cam drive wheel 76 through sequential mesh of first to fourth transmission wheels 71 to 74. These transmission wheels are using a part of a gear train also for use in a watch, thereby implementing both the size and thickness reduction of the transmission mechanism section 80.

These components, i.e., the step rotor 70a, and the first, third, and fourth transmission wheels 71, 73, and 74, are pivotally supported by the first and second frames 11 and 14 to be able to rotate. To the first frame 11, a transmission wheel shaft 75 is provided upright, and a tubular portion thereof is protruding upward, i.e., the direction along which the first and second cams 20 and 30 are provided. The transmission wheel shaft 75 is formed with a through hole, into which the tubular portion of the fourth transmission wheel 74 is inserted. The fourth transmission wheel 74 is also formed with a through hole, into which the shaft portion of the second transmission wheel 72 is inserted.

As to the second transmission wheel 72, one support shaft is pivotally supported by the second frame 14, and the other support shaft is pivotally supported by the through hole of the fourth transmission wheel 74. The rotation of the fourth transmission wheel 74 is transmitted to the cam drive wheel 76 being a center shaft via a fifth transmission wheel that is not shown.

The cam drive wheel 76 is pivotally supported by a through hole being inserted to the outer rim of the tubular portion of a transmission wheel shaft 75. The through hole of the cam drive wheel 76 is formed at the center thereof. The tubular portion of the cam drive wheel 76 is protruding in the direction along which the first and second cams 20 and 30 are disposed. The cam drive wheel 76 is pivotally supported, at the upper shaft portion, by a cam drive wheel support bearing 78 that is provided upright to the third frame 13. This third frame 13 is drilled with a hole for pivotally supporting the cam drive wheel support bearing 78. This hole is not going through the third frame 13, and the end portion of the cam drive wheel support bearing 78 is sealed by the third frame 13. As such, the third frame 13 is configuring an upper lid body of the tube unit 100. In the cam drive wheel 76, the rotation of the step rotor 70a is reduced in speed down to a predetermined value by the above-described transmission wheels. In this embodiment, the cam drive wheel 76 corresponds to an hour wheel of a watch.

Note that the cam drive wheel 76 is pivotally supported by the transmission wheel shaft 75 and the cam drive wheel support bearing 78. The distance between sections in charge of supporting is thus increased, thereby suppressing the amount of tilt of the cam drive wheel 76. As such, any lateral pressure to be applied to the shaft portion of the cam drive wheel 76 can be reduced. The lateral pressure is the one to be generated by the load torque of the first and second cams 20 and 30 that will be described later.

Described next is the relationship between the depression mechanism section 90 and the transmission mechanism section 80. The depression mechanism section 90 is disposed on the upper surface side of the first frame 11 with an overlay on the above-described transmission mechanism section 80. To the protruding tubular portion of the cam drive wheel 76, the second and first cams 30 and 20 are attached by insertion from the lower portion thereof in this order. Herein, the second cam 30 is pivotally supported by the cam drive wheel 76 with play therefrom, and the first cam 20 is fixed to the cam drive wheel 76 to be able to rotate theretogether.

A collar portion 76a of the cam drive wheel 76 is provided upright with a rotation stop shaft 77, and the protruding shaft portion thereof is inserted into a hole 20a formed to the first cam 20. The rotation stop shaft 77 is disposed at a position with a space from the cam drive wheel 76 (refer to FIG. 6 for the position on the plane), and the rotation stop shaft 77 provided as such favorably prevents the first cam 20 from idly running in a space with the cam drive wheel 76.

Note here that FIGS. 6 and 7 each show the state that the first and second cams 20 and 30 are both allowed to depress the tube 50. A spring section 33 provided to the second cam 30 is being free, and as shown in FIG. 6, the space from the tip end portion of a spring section 33, i.e., a friction engagement section 34, to the first cam 20 in the circumferential direction is set to be minimum required to release the engagement between the tip end portion of the spring section 33, i.e., the tip end portion of the friction engagement section 34 in the circumferential direction, and the first cam 20. This is aimed to prevent any possible pitch displacement between a finger depression section 32 and the first cam 20, i.e., finger depression portions 21a, 21b, and 21c, when the second cam 30 rotates before the first cam 20 due to some shock.

Around the first and second cams 20 and 30, the fourth frame 12 is provided. The fourth frame 12 is sandwiched between the third and first frames 13 and 11 described above, and the third and fourth frames 13 and 12 are formed as a piece using an adhesive or by welding with the tube 50 disposed therebetween.

In this embodiment, the third and fourth frames 13 and 12 being in a piece is referred to as tube guide frame, and the tube guide frame being securely fixing the tube 50 is referred to as the tube unit 100. The components not including the tube unit 100 are collectively referred to as the control unit 200.

As shown in FIG. 7, the fourth frame 12 is affixed with the IC tag 130 on the lower surface, i.e., on the side of the first frame 11. At the position opposing the IC tag 130, the reader 220 is disposed. The placement position of the IC tag 130 in the plane direction is assumed as being arbitrary in the outside direction of the depression mechanism section 90 and the transmission mechanism section 80 (refer also to FIG. 6).

Described next is the depression mechanism section 90 in this embodiment by referring to FIG. 6.

FIG. 6 is a plan view of a part of the micropump 10 of this embodiment. Note here that FIG. 6 shows that the micropump 10 is being in the state of constant driving, and is a perspective view of the third frame 13 viewed from the above. In FIG. 6, the depression mechanism section 90 is configured to include the first and second cams 20 and 30, and seven fingers 40 to 46. The first and second cams 20 and 30 here are being fixed to the cam drive wheel 76 or pivotally supported thereby. The seven fingers 40 to 46 each serve as a depression member, and are disposed between the tube 50 and the first and second cams 20 and 30 radially from the rotation center P of the cam drive wheel 76. The fingers 40 to 46 are disposed at regular intervals.

The first cam 20 is fixed, at the center portion, to the shaft portion of the cam drive wheel 76. The first cam 20 has three protrusion portions at the outer rim portion, and is formed with a finger depression section at the outermost portion. The finger depression section is configured by the three finger depression portions 21a to 21c, which are formed concentrically to the rotation center P at the same distance therefrom. The finger depression portions 21a and 21b share the same circumferential pitch and the outside shape, and the finger depression portions 21b and 21c also share the same circumferential pitch and the outside shape. The space between the finger depression portions 21a and 21c is twice as the circumferential pitch between the finger depression portions 21a and 21b or the finger depression portions 21b and 21c.

The finger depression portion 21a is provided with, at the base portion, a concave portion formed concentrically to the rotation center P of the cam drive wheel 76, i.e., the same as the rotation center of the first and second cams 20 and 30. As to this concave portion, the bottom surface thereof serves as a second cam placement surface 25 onto which the spring section 33 of the second cam 30 is placed. Such finger depression portions 21a to 21c are each formed with, in a row, a finger depression sloped surface 22 and an arc section 23 on the concentric circle about the rotation center P. This arc section 23 is disposed at a position with a space from the fingers 40 to 46 not to depress the fingers 40 to 46.

The finger depression portions 21a, 21b, and 21c are each connected, at one end portion, to the arc section 23 with a linear section 24, which is an extension from the rotation center P. At the lower portion of the first cam 20, the second cam 30 is pivotally supported by a shaft portion of the cam drive wheel 76, and is attached by insertion to the shaft portion of the cam drive wheel 76 to be able to rotate.

The second cam 30 is configured to include the finger depression section 32, and a finger depression sloped surface 31. The finger depression section 32 is in the same shape as the above-described finger depression portions 21a, 21b, and 21c of the first cam 20, and the finger depression sloped surface 31 is in the same shape as the finger depression sloped surface 22. The second cam 30 is also formed with the spring section 33 serving as an elastic section protruding like an island. This spring section 33 is provided concentrically to the rotation center P, and is so shaped as to fit in the concave portion formed to the first cam 20 described above, i.e., the second cam placement surface 25. From the underside of the tip end of the spring section 33, the friction engagement section 34 of a cylindrical shape is protruding.

The second cam 30 is provided with, on the side opposite to the spring section 33 in the plane direction, an arc section 36 and a linear section 35. The arc section 36 is of the same diameter as that of the arc section 23 provided to the first cam 20 described above, and the linear section 35 is for connection with the rotation center P, which connects the arc section 36 and the finger depression section 32.

Described now is the relationship between the first and second cams 20 and 30. The first cam 20 is fixed to the shaft portion of the cam drive wheel 76, thereby rotating in the direction of an arrow R as the cam drive wheel 76 rotates. The second cam 30 is fit to the shaft portion of the cam drive wheel 76 with play therefrom, and thus do not rotate together with the first cam 20. However, the rotation force of the first cam 20 is transmitted to a first cam engagement section 38 from a second cam engagement section 26 being engaged thereto, and thus the second cam 30 rotates together with the first cam 20, thereby being put into the state of being able to depress the fingers 40 to 46. The first cam engagement section 38 is the one disposed at the end portion of the second cam 30, and the second cam engagement section 26 is disposed at the end portion of the finger depression portion 21c of the first cam 20.

In such a state, the engagement is released between the spring section 33 of the second cam 30 and the second cam placement surface 25 of the first cam 20, and the first and second cams 20 and 30 look as if they are configuring a single cam including the finger depression portions 21a to 21c and 32 at four positions.

Although not shown, the finger depression portions 21a to 21c and 32 are formed concentrically to the rotation center P, and are each so set as to be of a size with which any two adjacent fingers can abut a finger depression area formed by the concentric circle.

At a position with a space from the first and second cams 20 and 30, the tube 50 is disposed for making a fluid to flow therethrough. The tube 50 is elastic, and is formed by silicon rubber in this embodiment. The tube 50 is attached to a tube guide groove 121 formed to the fourth frame 12, and one end portion thereof is the outflow port 53 from which a fluid flows out to the outside. The outflow port 53 is protruding outside of the micropump 10, i.e., the tube unit 100. The other end portion of the tube 50 is an inflow port 52 from which the fluid flows into, and is connected to the connection tube 55. The end portion of the connection tube 55 is linked to the reserver 60 (not shown) housing therein the fluid.

The tube 50 is attached to the tube guide groove 121 at the area to be depressed by the fingers 40 to 46. The tube guide groove 121 is the one formed concentrically to the rotation center P. At the space among the tube 50, and the first and second cams 20 and 30, the fingers 40 to 46 are disposed radially with respect to the rotation center P.

The fingers 40 to 46 are each inserted into a finger retention hole 16a formed to a finger retention frame 16. The fingers 40 to 46 are each of the same shape, and thus the finger 44 is exemplarily described. The finger 44 is configured to include a cylindrical shaft portion 44a, a collar portion 44c, and an abutment portion 44b. The collar portion 44c is disposed at one end portion of the shaft portion 44a, and the abutment portion 44b is the hemispherically-rounded other end portion of the shaft portion 44a. The collar portion 44c is the depression section for depressing the tube 50, and the abutment portion 44b is the depression section to be depressed by the first or second cam 20 or 30.

By referring to FIG. 8, described next is the relationship between the finger 44 and the finger retention frame 16. In FIG. 8, the finger 44 is formed with an operation groove 47 between the collar portion 44c and the abutment portion 44b. The finger retention frame 16 is formed with a protrusion portion 16b in the operation groove 47. The finger 44 is able to slide to move back and forth in the shaft direction in a range where the end surface of the protrusion portion 16b in the shaft direction abuts the end surface of the operation groove 47 in the shaft direction each other.

The protrusion portion 16b serves not to allow the finger 44 fall off unless it is forcefully pulled out.

Note here that the finger retention frame 16 is elastic, and for insertion of the finger 44 into the finger retention hole 16a, the protrusion portion 16b is put back to its original protrusion shape when reaching the operation groove 47 due to its elastic deformation. As such, the finger 44 is prevented from falling off from the finger retention frame 16.

The finger retention frame 16 is attached to the first frame 11 while being inserted with the fingers 40 to 46. For attachment of the finger retention frame 16, guide pins 16c and 16d protruding from the bottom surface of the finger retention frame 16 are respectively pressed into fixing holes formed to the first frame 11.

The fingers 40 to 46 are allowed to move back and forth along the finger retention hole 16a, and are pressed by the first and second cams 20 and 30 in the outside direction. As such, the fingers 40 to 46 depress the tube 50 with a tube guide wall 122 of the tube guide groove 121, thereby compressing a liquid flow section 51. The center position of each of the fingers 40 to 46 in the cross sectional direction are substantially the same as the center of the tube 50.

As such, the micropump 10 of this embodiment is configured by two main units, i.e., the control unit 200 equipped with the depression mechanism section 90 including the first and second cams 20 and 30 and the fingers 40 to 46, and the tube unit 100 configured by the tube 50, and the third and fourth frames 13 and 12, i.e., tube guide frame. These unit are detachably attached to each other by the attachment/detachment mechanism section 150.

The attachment/detachment mechanism section 150 is described by referring to FIG. 8 (refer to FIG. 6 for the position on the plane surface). The outer rim portion of the fourth frame 12 is provided with, at two positions, a hook 12a that is extending along the outer rim side surface of the first frame 11. The hook 12a is formed with a latch portion 12b at the tip end portion, and is engaged with a latch concave portion 11a formed to the first frame 11.

The hook 12a is formed elastic. Therefore, for attachment of the tube unit 100 to the control unit 200, the hook 12a is elastically deformed, and is put back to its original shape when the latch portion 12b reaches the latch concave portion 11a so that the tube unit 100 is attached to the control unit 200. To remove the tube unit 100 from the control unit 200, the hook 12a is deformed toward the outside to release the engagement between the latch portion 12b and the latch concave portion 11a. As such, the provision of the attachment/detachment mechanism section 150 eases the attachment/detachment of the tube unit 100 to/from the control unit 200.

Described next are the effects related to the discharge of a liquid in this embodiment by referring to FIG. 6. In FIG. 6, the finger 44 is depressed by the finger depression section 32 of the second cam 30, and the finger 45 is abutting a junction portion between the finger depression section 32 and the finger depression sloped surface 31, thereby closing the tube 50. The finger 46 is depressing the tube 50 on the finger depression sloped surface 31 but the depression by the finger 46 is smaller than that by the finger 44, and thus the tube 50 is not completely closed.

The fingers 41 to 43 are all located in the range of the arc section 36 of the second cam 30, i.e., at the initial positions free from depression. The finger 40 is abutting the finger depression sloped surface 22 of the first cam 20, but at this position, the tube 50 is not yet closed.

From such a position, when the first and second cams 20 and 30 are rotated to a further degree in the direction of the arrow R, the finger depression section 32 of the second cam 30 starts depressing the fingers 45 and 46 in this order so that their corresponding portions of the tube 50 become closed. The finger 44 then becomes free from the finger depression section 32 so that the closure of the tube 50 is released for the portion. At the portion of the tube 50 where being free from the closure by the finger, or at the portion of the tube 50 where being not yet closed, the liquid is flowing into the liquid flow section 51 from the reserver 60.

When the first cam 20 is rotated to a further degree, the finger depression sloped surface 22 starts depressing sequentially the fingers 40, 41, 42, and 43 in this order. When the finger depression sloped surface 22 reaches the finger depression portion 21c, the tube 50 is closed.

With such an operation repeatedly performed, the liquid is made to flow from the side of the inflow port 52 to the side of the outflow port 53, thereby being discharged from the outflow port 53, i.e., in the direction of an arrow F.

At this time, to the finger depression section of the first cam 20 and that of the second cam 30, two of the fingers are abutting, and when these sections move to the positions for depressing the next finger, one of the fingers is accordingly depressed thereby. Such repetition of states, i.e., the state that two fingers are depressed and the state that one finger is depressed, forms the state in which at least one finger is always closing the tube 50. As such, even at the time of switching of depressing finger when the first and second cams 20 and 30 are sequentially performing finger depression, any one of the fingers is unfailingly depressed and thus the tube 50 is closed thereby. This accordingly prevents any back-flow of a fluid, and enables the continuous flow of the fluid.

Described next is the state in which the finger(s) close the tube 50 by referring to FIG. 8. In FIG. 8, exemplified is the state in which the finger 44 closes the tube 50. In FIG. 8, the tube 50 is retained at the position shown in FIG. 8 with a large portion in the cross sectional direction being inserted into the tube guide groove 121 provided to the fourth frame 12, i.e., indicated by a chain double-dashed line in the drawing.

The fourth frame 12 is provided with a concave section 125 of a size in which the collar portion 44c is allowed to move. At the lower portion of the tube guide wall 122 provided upright to the tube guide groove 121, a concave portion is formed to serve as an area into which the tube 50 is allowed to deform when it is closed.

The third frame 13 is formed with, at the position corresponding to the tube guide groove 121, a groove of a size to which the tube 50 can be attached. The third frame 13 is also formed with a concave section 140 corresponding to the concave section 125, and another concave section serving as an area into which the tube 50 is allowed to deform when it is closed. When the tube depression section of the first cam 20 or that of the second cam 30 is depressing no finger, the liquid flow section 51 of the tube 50 is not closed. The position of the finger 44 at this time is indicated by a chain double-dashed line.

The finger 44 is closed by the finger depression section 32, thereby closing the tube 50. Thereafter, when the finger 44 is moved backward and when the tube 50 thus becomes free from the depression thereby, the liquid flow section 51 is put back to its original shape. At this time, the tube 50 is put back to its original shape, i.e., back to its initial position indicated by a chain double-dashed line, by the tube guide section 123 partially protruding to the concave section 125 of the fourth frame 12.

The tube guide section 123 is formed with a sloped surface in the direction of the tube 50, and helps the tube 50 to be back to its initial position. As shown in FIG. 6, this tube guide section 123 is provided at four positions, i.e., in the vicinity of the outside of the finger 40, between the fingers 41 and 42, between the fingers 44 and 45, and in the vicinity of the outside of the finger 46. The tube guide section 123 serves to help the tube 50 to be back in shape without fail, i.e., from the position being closed to the position being free from depression.

According to the first embodiment described above, the tube unit 100 and the control unit 200 can be detachably attached to each other by the attachment/detachment mechanism section 150. Accordingly, when the reserver 60 is needed to be replaced because a liquid therein is running out, replacing only the tube unit 100 being less expensive than the control unit 200 including various components, i.e., the depression mechanism section 90, the transmission mechanism section 80, the motor 70, the reader 220, the display section 240, the operation section 230, and the control circuit section 210, will favorably lead to the reduction of the running cost.

When any one specific position of the elastic tube 50 is continuously depressed, i.e., pressed hard, by the fingers 40 to 46 for a long period of time, the elasticity will be lost so that the tube 50 may be deformed. In consideration thereof, until the use of the micropump 10, the second cam 30 is kept at the position where the tube 50 is free from the depression by the fingers 40 to 46, and after driving of the micropump 10, the second cam 30 is moved to the position where the tube 50 is depressed by the fingers 40 to 46. This accordingly prevents any possible deformation of the tube 50 resulted from the long-time depression at the same position.

Moreover, if the micropump 10 is kept stored or used for a long period of time, or if the operation of the micropump 10 is stopped halfway through for a long time, the tube 50 may be changed in internal diameter or deteriorated. However, this problem can be favorably solved by throwing away the tube 50, i.e., the tube 50 is for one time use only, so that the tube can be replaced at low cost with another tube with an appropriate range of internal diameter and elasticity.

Further, because the tube 50 is formed as a piece with the tube guide frame, the replacement thereof is easily done even by a not-skilled user.

Still further, the tube unit 100 stores, in an IC tag serving as a tube individual data storage section, the tube individual data including the internal diameter of the tube 50 or the tube contents of the peristaltic section, and the identification data of the tube unit 100. This tube individual data is read by the reader 220 so that the motor is driven and controlled based thereon. As such, the resulting micropump becomes able to discharge a liquid with high accuracy in accordance with the internal diameter of the tube in use.

Still further, the identification data of the tube unit 100 is provided to the control unit 200 while the tube unit 100 is being attached to the control unit 200, thereby favorably preventing a user from attaching any wrong tube unit 100.

Still further, the control unit 200 is configured to include the display section 240 and the operation section 230. With this configuration, the display section 240 enables a user to always check the state of the micropump 10, i.e., the state of drive control, the setting of drive requirements, and the state of driving. Using the setting operation section 250, the user can make settings of any needed requirements with ease.

Alternatively, the operation section 230 may be so configured that the operation of the setting operation section 250 enables direct inputs of the tube individual data to the control circuit 210. If this is the configuration, even if no input can be made from the tube individual data storage section, i.e., the IC tag 130, to the tube individual data processing section, i.e., the reader 220, the operation section 230 is allowed to make an input of the tube individual data directly to the control circuit 210 so that the micropump can be used based on the tube individual data.

As another alternative configuration, the reader/writer unit may be provided outside of the micropump 10. With such a configuration, the reader/writer unit provided outside as such detects the attachment between the tube unit 100 and the control unit 200. The reader/writer unit also reads the tube individual data stored in the IC tag 130, and writes the data into the control unit 200, i.e., the tube individual data storage section, using radio or cable communications means.

Alternatively, the control unit 200 may be provided with the IC tag 130, and the reader/writer unit provided outside of the micropump 10 may read the tube individual data for writing using radio communications means.

With such a configuration, there is no need to include the reader/writer unit in the micropump 10, thereby being able to simplify the configuration of the tube unit 100 and that of the control unit 200. Accordingly, there are various effects such as the size reduction of the resulting micropump 10, the reduction of the running cost, and the reduction of the power consumption as with no reader/writer unit.

Second Embodiment

Described next is a micropump in a second embodiment of the invention by referring to the accompanying drawings. In the second embodiment, a tube unit is provided with a depression mechanism section, and the remaining components are almost the same as those in the first embodiment described above. Therefore, described here are only those different from the first embodiment, and any components similar to those in the first embodiment are provided with the same reference numerals.

FIG. 9 is a diagram for illustrating the schematic configuration of the micropump of the second embodiment. In FIG. 9, the micropump 10 is configured by two units, i.e., the tube unit 100 and the control unit 200. These units are driven while being detachably attached to each other by the attachment/detachment mechanism section 150, and discharge a liquid.

The tube unit 100 is configured to include the tube 50, the tube guide frame, the depression mechanism section 90, and the IC tag 130 serving as the tube individual data storage section. The tube guide frame here is the one configured by the third and fourth frames 13 and 12. Accordingly, the control unit 200 is of the configuration similar to that of the first embodiment but not including the depression mechanism section 90.

Described next is the tube unit 100, the depression mechanism section 90, and the attachment/detachment mechanism section 150 by referring to the accompanying drawings.

FIG. 10 is a partial cross sectional view of the tube unit, the depression mechanism section, and the attachment/detachment mechanism section. Described first is the depression mechanism section. In FIG. 10, the transfer wheel shaft 75 is fixed to the center portion of the first frame 11, and to the tubular portion of the transfer wheel shaft 75 protruding upward, the cam drive wheel 76 is pivotally supported by a through hole formed at the center being inserted into the outer rim of the tubular portion of the transmission wheel shaft 75. In the cam drive wheel 76, the tubular portion is protruding in the direction where the first and second cams 20 and 30 are provided. The upper shaft portion of the cam drive wheel 76 is pivotally supported by the cam drive wheel support bearing 78 provided upright to the third frame 13.

To the protruding tubular portion of the cam drive wheel 76, the second and first cams 30 and 20 are inserted from below in this order. In this example, the second cam 30 is pivotally supported by the cam drive wheel 76 with play therefrom, and the first cam 20 is pivotally supported so as to rotate as a piece with the cam drive wheel 76.

The tube guide frame is fixedly held in such a manner as to sandwich the tube 50 between the fourth and third frames 12 and 13. This configuration is the same as that of the first embodiment. The fourth frame 12 is formed with a plurality of finger guide grooves 126 linked to the tube guide groove 121, and the finger guide grooves 126 are respectively attached with the fingers 40 to 46, e.g., the finger 44 is exemplarily shown in FIG. 10. The upper portions of the fingers 40 to 46 are held by the third frame 13. The first frame 11, the fourth frame 12, and the third frame 13 are attached, on their interface, with the tube 50, the fingers 40 to 46, and the first and second cams 20 and 30. The attachment result is then subjected to thermal welding, bonding, or screwing to be a piece so that the tube unit 100 is formed. FIG. 7 is referred to for the relationship between the transmission mechanism section 80 (not shown) and the depression mechanism section 90.

Described next is the attachment/detachment mechanism section 150 (refer to FIG. 6 for the position on the plane). Also in this embodiment, the attachment/detachment mechanism section 150 is exemplified by the configuration using the hook mechanism. At the outer rim portion of the first frame 11 located at the bottom portion of the tube unit 100, a hook 11*b* is provided, at two portions, by extending along the outer rim surface of the second frame 14. The tip end portion of the hook 11*b* is formed with a latch portion 11*c*, which is engaged with a latch concave portion 14*a* formed to the second frame 14.

The hook 11*b* is formed elastic. Therefore, for attachment of the tube unit 100 to the control unit 200, the hook 11*b* is elastically deformed, and is put back to its original shape when the latch portion 11*c* reaches the latch concave portion 14*a* so that the tube unit 100 is latched by the control unit 200. To remove the tube unit 100 from the control unit 200, the hook 11*b* is deformed toward the outside to release the engagement between the latch portion 11*c* and the latch concave portion 14*a*. As such, the provision of the attachment/detachment mechanism section 150 eases the attachment/detachment of the tube unit 100 to/from the control unit 200.

Note here that the configuration of the IC tag 130 being the tube individual data storage section and that of the reader 220 being the tube individual data processing section are the same as those in the first embodiment.

The second frame 14 is fixed to the shelf-like section 202 (refer to FIG. 2), which is protruding from upper surface of the base 201 of the control unit 200.

As such, according to the second embodiment described above, the tube unit 100 is provided with the depression mechanism section 90 including the first and second cams 20 and 30, and the fingers 40 to 46. This configuration favorably enables to prevent any possible relative displacement between the tube 50 and the depression mechanism section 90, especially enables to correctly manage the relative positioning of the tube 50 and the fingers 40 to 46. This leads to the effects of being able to transmit the correct peristaltic movement to the tube 50, and to correctly maintain the amount and speed of discharge of a liquid.

Third Embodiment

Described next is a third embodiment of the invention by referring to the accompanying drawings. In the third embodiment, a tube unit is provided with a depression mechanism section, a transfer mechanism section, and a motor. The remaining components are the same as those in the first embodiment described above. Therefore, described here are only those different from the first embodiment, and any components similar to those in the first embodiment are provided with the same reference numerals.

FIG. 11 is a diagram for illustrating the schematic configuration of a micropump of the third embodiment, and FIG. 12 is a partial cross sectional view of the tube unit and a control unit, showing their relationship. Described first is the configuration of the micropump by referring to FIG. 11. In FIG. 11, the micropump 10 is configured by two units, i.e., the tube unit 100 and the control unit 200. These units are driven while being detachably attached to each other by the attachment/detachment mechanism section 150, and discharge a liquid.

The tube unit 100 is configured to include the tube 50, the tube guide frame, the depression mechanism section 90, the transmission mechanism section 80, the motor 70, and the IC tag 130 serving as the tube individual data storage section. The tube guide frame here is the one configured by the third and fourth frames 13 and 12. Accordingly, the control unit 200 is of the configuration similar to that of the first embodiment but not including the depression mechanism section 90, the transmission mechanism section 80, and the motor 70.

By referring to FIG. 12, described next is the tube unit 100, the control unit 200, and the attachment/detachment mechanism section 150. The second frame 14, the first frame 11, the fourth frame 12, and the third frame 13 are attached, on their interface, with the tube 50, the fingers 40 to 46 (refer to FIG. 6), the depression mechanism section 90, the transmission mechanism section 80, and the IC tag 130. The attachment result is then subjected to thermal welding, bonding, or screwing to be a piece so that the tube unit 100 is formed. The tube unit 100 is fixed to the shelf-like section 202 (refer to FIG. 2) protruding from the upper surface of the base 201 of the control unit 200. The depression mechanism section 90 and the transmission mechanism section 80 are similar in configuration to those of the first embodiment (refer to FIG. 7), and thus are not described twice.

Described next is the attachment/detachment mechanism section 150 (refer to FIG. 6 for the position on the plane). Also in this embodiment, the attachment/detachment mechanism section is exemplified by the configuration using the hook mechanism. At the outer rim portion of the second frame 14 located at the bottom portion of the tube unit 100, a hook 14b is provided, at two portions, by extending along the outer rim surface of the shelf-like section 202. The tip end portion of the hook 14b is formed with a latch portion 14c, which is engaged with a latch concave portion 202a formed to the shelf-like section 202.

The hook 14b is formed elastic. Therefore, for attachment of the tube unit 100 to the control unit 200, the hook 14b is elastically deformed, and is put back to its original shape when the latch portion 14c reaches the latch concave portion 202a so that the tube unit 100 is attached to the control unit 200. To remove the tube unit 100 from the control unit 200, the hook 14b is deformed toward the outside to release the engagement between the latch portion 14c and the latch concave portion 202a. As such, the provision of the attachment/detachment mechanism section 150 eases the attachment/detachment of the tube unit 100 to/from the control unit 200.

Note here that the configuration of the IC tag 130 being the tube individual data storage section and that of the reader 220 being the tube individual data processing section are the same as those in the first embodiment.

As such, according to the third embodiment described above, the tube unit 100 is further provided with the depression mechanism section 90, the transmission mechanism section 80, and the motor 70, and the control unit 200 is provided with the display section 240, the operation section 230, and the battery 260. Accordingly, the tube unit 100 includes the drive section in its entirety, and this means that the components, i.e., the depression mechanism section 90, the transmission mechanism section 80, and the motor 70, are not separately provided. This thus eases a user's attachment between the tube unit 100 and the control unit 200, and causes no problem related to engagement among the drive components and no reduction of assembly.

What is more, the motor 70 for use with the micropump 10 in the embodiment of the invention is a stepper motor of the size of a watch for the purpose of size reduction and power saving. This thus allows to replace the motor 70 at the same time as the replacement of the tube unit 100 considering the heavy load driving of the motor so that the improvement of the reliability can be achieved.

Fourth Embodiment

Described next is a micropump of a fourth embodiment of the invention by referring to the accompanying drawings. Unlike the above-described first to third embodiments in which the IC tag 130 and the reader 220 both serve as the reader/writer unit, in the fourth embodiment, tube unit 100, i.e., tube individual storage section, includes a transmission/reception control circuit section and a radio antenna, and the control unit 200, i.e., tube individual data processing section, includes a transmission/reception data processing section and a radio antenna. The remaining components are similar to those in the first embodiment, and thus are not described twice.

FIG. 13 is a diagram showing the schematic configuration of the tube individual data storage section and the tube individual data processing section, and FIG. 14 is a partial cross sectional view thereof, showing their schematic configuration. In FIGS. 13 and 14, a tube individual data storage section 280 is configured to include, on the surface of a substrate 285, a radio antenna 281, and a transmission/reception control circuit 282. The transmission/reception control circuit 282 is configured to include a transmission/reception circuit 283 for control over data transmission and reception, and a storage circuit 284 for storage of data. The storage circuit 284 is exemplified by a nonvolatile memory.

For making an input of tube individual data to the tube individual data storage section 280, radio communications will do from a writing unit 270 that is separately provided. Alternatively, the tube individual data may be stored in advance in the transmission/reception control circuit 282.

The tube individual data processing section 290 is configured to include, on the surface of a substrate 295, a radio antenna 291 and a transmission/reception data processing section 292. The transmission/reception data processing section 292 is configured to include a transmission/reception circuit 293 for control over data transmission and reception, and a storage circuit 294 for storage of data. The storage circuit 294 is exemplified by a nonvolatile memory. Also provided is a data processing circuit 211 for data input into the control circuit section 210 after data processing of any incoming tube individual data.

In FIG. 14, the substrate 285 of the tube individual data storage section 280 is fixed to the lower surface side of the fourth frame 12 of the tube unit 100 using fixing means such as adhesion.

The substrate 295 of the tube individual data processing section 290 is fixed to the upper surface side of the second frame 14 of the control unit 200 using fixing means such as adhesion. In FIG. 14, the tube individual data storage section 280 and the tube individual data processing section 290 are disposed opposing each other. However, because the tube individual data storage section 280 and the tube individual data processing section 290 are connected to each other using radio communications means, as long as the components are disposed within a range of radio transmission, their placement positions are not specifically restricted.

The transmission of the tube individual data is detected by a connection terminal (not shown) or others based on the state of attachment between the tube unit 100 and the control unit 200, i.e., whether these units are in any predetermined state of attachment. An output command signal is then output directly from the tube individual data storage section 280 or from the tube individual data processing section 290 so that the tube individual data is transmitted from the tube individual data storage section 280.

As an alternative configuration, in the state that the tube unit 100 is attached to the control unit 200, the output command signal may be output to the tube individual data storage section 280 through operation of the tube individual data acquisition button 233 (refer to FIG. 1) provided to the control unit 200, thereby transmitting the tube individual data from the tube individual data storage section 280.

As such, the fourth embodiment can derive the effects similar to the configuration of the above-described first embodiment, i.e., the configuration of including the IC tag 130 and the reader 220, and the effects of being able to reduce the restrictions in terms of layout design as with no restrictions of placement position of the tube individual data storage section 280 and that of the tube individual data processing section 290.

Fifth Embodiment

Described next is a fifth embodiment of the invention by referring to the accompanying drawings. Unlike the above-described first to fourth embodiments in which the reader/writer unit is using radio communications means, a direct connection is established using an input/output terminal in the fifth embodiment. The remaining components are similar to those in the first embodiment, and thus are not described twice.

FIG. 15 is a partial cross sectional view of the tube individual data storage section and the tube individual data processing section, showing their schematic configuration. In FIG. 15, the reader/writer unit is configured to include the tube individual data storage section 280 in which the substrate 285 carries thereon the transmission/reception control circuit 282, and the tube individual data processing section 290 in which the substrate 295 carries thereon the transmission/reception data processing section 292. The transmission/reception control circuit 282 is configured to include a transmission/reception circuit and a storage circuit, which are not shown. The storage circuit can be a nonvolatile memory, and is storing therein the tube individual data in advance.

Alternatively, the tube individual data storage section 280 may include a resistance or capacitor being set to a value corresponding to the tube individual data. Through attachment of the tube unit 100 to the control unit 200, the control unit 200 may be so configured as to read the tube individual data from a data table based on a frequency or a voltage value provided by the storage circuit including the resistance or the condenser described above.

The substrate 285 of the tube individual data storage section 280 is fixed to the lower surface side of the fourth frame 12 of the tube unit 100 using fixing means such as adhesion.

Although not shown, the transmission/reception data processing section 292 is configured to include a reading circuit section and a data processing circuit. The reading circuit section serves to read the tube individual data stored in the storage circuit of the tube individual data storage section 280. The substrate 295 of the tube individual data processing section 290 is fixed to the upper surface side of the second frame 14 of the control unit 200 using fixing means such as adhesion.

To the substrate 295, a connection electrode 296 is extended for connection with the transmission/reception data processing section 292, and onto the surface of the connection electrode 296, an input/output terminal 300 is fixed using fixing means such as solder or conductive adhesive. The input/output terminal 300 is a metal terminal bent into the shape substantially like a letter of U. The tip end portion of the substantially-U-shaped portion serves as a contact section 301 with the tube individual data storage section 280.

Also to the substrate 285 of the tube individual data storage section 280, a connection electrode 303 is extended for connection with the transmission/reception control circuit 282. When the tube unit 100 is attached to the control unit 200, the contact section 301 of the input/output terminal 300 comes into contact with the connection electrode 303 so that a connection is established between the tube individual data storage section 280 and the tube individual data processing section 290. With a connection established between the tube individual data storage section 280 and the tube individual data processing section 290 as such, the predetermined state of attachment is detected so that the tube individual data is forwarded from the tube individual data storage section 280 to the tube individual data processing section 290.

Alternatively, through operation of the tube individual data acquisition button 233 (refer to FIG. 1), a tube individual data acquisition signal may be acquired from the tube individual data storage section 280 to the tube individual data processing section 290.

As such, data provision to the control unit 200 is performed from the storage circuit of the transmission/reception control circuit 282 storing in advance the tube individual data via the input/output terminal 300. This thus enables reading of the tube individual data without fail, and simplifies the circuit configuration as is required to include only the input/output terminal 300.

Sixth Embodiment

Described next is a sixth embodiment of the invention. In the sixth embodiment, for use as the reader/writer unit, the tube unit 100 includes a tube individual data display section, and the control unit 200 includes an optical reading/processing unit. The remaining components other than the reader/writer unit are the same as those in the first embodiment, and thus are not described and shown twice.

Herein, the tube individual data display section is a two-dimensional code typified by barcode, and the internal diameter of the tube and the quantity of contents of a peristaltic section are previously recorded onto a sheet by two-dimensional codes. When the tube individual data display section is a barcode as such, the reading/writing device is a barcode reader for optically reading barcode fonts.

The tube individual data display section is affixed to the tube unit, and at the position opposing the tube individual data display section of the control unit, the reading/processing unit is disposed. The reading/processing unit optically reads the tube individual data, and subjects the data to processing before input to the control circuit section.

According to the sixth embodiment described above, with such a configuration in which the tube individual data display section being a barcode, the tube unit 100 is attached only by a label printed with a barcode font. As such, the tube individual data display section does not become thick that much. Moreover, the barcode reader can be of general configuration.

Seventh Embodiment

Described next is a seventh embodiment of the invention. Unlike the above-described first to sixth embodiments in which a battery being a power supply is attached to the control unit, a battery is attached to the tube unit in the seventh embodiment.

Although not shown, a battery is attached to the tube unit, and is held by two battery terminals. The battery terminals are each protruded to the side of the control unit. The control unit is provided with a power supply terminal for connection to the control circuit section, and the battery terminals and the power supply terminal are connected together while the tube unit is being attached to the control unit so that the power is input to the control circuit section.

Alternatively, the battery may be fixed to the tube unit, and held thereby detachably.

Herein, if the power supply is a small-sized coin or button battery, the micropump can be easily carried around. However, with the small battery capacity, the battery replacement is required. Such battery replacement is made together with the tube at the time of replacement of the tube unit so that any possible problem such as battery exhaustion can be prevented during the use of the micropump.

Furthermore, the tube unit 100 and the control unit 200 can be separately handled, thereby achieving the cost reduction for the resulting micropump. The components in the tube unit 100 and those in the control unit 200 can be changed in combination depending on the components in the other unit so that the component selection can be made in accordance of a user's state of use.

While the invention has been described in detail, the foregoing description is in all aspects illustrative and not restrictive. It is understood that numerous other modifications and variations can be devised without departing from the scope of the invention.

For example, in the first embodiment described above, the control unit 200 is including the depression mechanism section 90. Alternatively, out of the components in the depression mechanism section 90, the fingers 40 to 46 may be provided to the tube unit 100, and the first and second cams 20 and 30 may be provided to the control unit 200.

Moreover, exemplified in the first to seventh embodiments is the configuration of using the battery 260 as a power supply. As an alternative configuration, a power supply cable using utility power may be used for the control unit 200.

The micropump of the embodiments of the invention is mounted in or out of various types of mechanical devices, and can be used to transfer a fluid such as water, salt water, liquid preparations, oil, aromatic liquid, and ink, or a gas. The micropump can be solely used to make the fluid flow or to supply the fluid.

The entire disclosure of Japanese Patent Application Nos: 2006-330156, filed Dec. 7, 2006 and 2007-264206, filed Oct. 10, 2007 are expressly incorporated by reference herein.

What is claimed is:

1. A micropump of a peristaltic type that continuously transfers a fluid through depression of an elastic tube, the micropump comprising:

a tube unit configured to at least include the tube in which the fluid is transferred, a tube guide frame that fixedly holds the tube, and a tube individual data storage section that stores therein tube individual data;

a depression mechanism section having a rotation cam that sequentially deforms portions of the tube to transfer the fluid along a length of the tube;

a control unit that is attachable/detachable to/from the tube unit, and at least includes a control circuit section that drives and controls the tube and control units, via a transmission mechanism section, a motor for driving the depression mechanism section, and a tube individual data processing section including a reader/writer unit that reads the tube individual data for data processing thereof; and a power supply that makes an electrical supply to the control unit, wherein the reader/writer unit detects attachment of the tube unit to the control unit and sends the tube individual data to the control unit, the tube individual data is used as a basis for controlling and driving the tube and control units, the rotation cam sequentially depresses a plurality of depression members with respect to the tube from an inflow side to an outflow side thereof, the rotation cam is configured by a first cam that is fixed to a center shaft and a second cam that is pivotally supported by the center shaft, and the second cam is able to move from a position where the tube is free from the depression members to a position where the tube can be depressed thereby.

2. The micropump according to claim 1, wherein the tube individual data serves to correct a variation of a quantity of discharge of the fluid.

3. The micropump according to claim 1, wherein the control unit further includes:

a display section that at least displays thereon the tube individual data and a discharge program of the fluid; and an operation section that operates according to the tube individual data and the discharge program of the fluid.

4. The micropump according to claim 1, wherein the control unit further includes:

a display section that at least displays thereon the tube individual data and a discharge program of the fluid; and an operation section for operating the control unit, and the power supply is contained within the control unit.

5. The micropump according to claim 1, wherein the power supply is contained within the tube unit.

6. The micropump according to claim 1, wherein the control unit is configured to include the depression mechanism section, the transmission mechanism section, and the motor.

7. The micropump according to claim 1, wherein the tube unit is configured to include the depression mechanism section, and the control unit is configured to include the transmission mechanism section and the motor.

8. The micropump according to claim 1, wherein the tube unit is configured to include the depression mechanism section, the transmission mechanism section, and the motor.

9. The micropump according to claim 1, wherein the reader/writer unit is configured to include a transmission/reception control circuit section and a radio antenna that are provided to the tube individual data storage section for transmission of the tube individual data to the tube individual data processing section, and a transmission/reception data processing section and another radio antenna that are provided to the tube individual data processing section, and receive the tube individual data when the tube unit is attached to the control unit for data processing.

10. The micropump according to claim 1, wherein the reader/writer unit is configured to include a storage circuit that is provided to the tube individual data storage section for storage of the tube individual data, and an input/output terminal provided to the tube individual data processing section, and the reader/writer unit establishes a connection to the storage circuit in response to attachment of a reading circuit section that reads the tube individual data stored in the storage circuit, a data processing section that processes the tube individual data, and the tube unit to the control unit.

11. The micropump according to claim 1, wherein the reader/writer unit is configured to include a tube individual data display section that is provided to the tube individual data storage section for display of the tube individual data, and a reading/processing unit that is provided to the tube individual data for optical reading and data processing of the tube individual data when the tube unit is attached to the control unit.

12. A tube unit that is attachable/detachable to/from a control unit that drives and controls a micropump of a peristaltic type that continuously transfers a fluid through depression of an elastic tube by a depression mechanism section, the tube unit comprising:

the tube in which the fluid is transferred;
a tube guide frame that fixedly holds the tube; and
a tube individual data storage section that stores therein tube individual data, wherein
the depression mechanism section has a rotation cam that sequentially deforms portions of the tube to transfer the fluid along a length of the tube,
the rotation cam sequentially depresses a plurality of depression members with respect to the tube from an inflow side to an outflow side thereof,
the rotation cam is configured by a first cam that is fixed to a center shaft and a second cam that is pivotally supported by the center shaft, and
the second cam is able to move from a position where the tube is free from the depression members to a position where the tube can be depressed thereby.

13. A control unit that is attachable/detachable to/from a tube unit, which includes an elastic tube, in a micropump of a peristaltic type that continuously transfers a fluid through depression of the tube by a depression mechanism section, the control unit comprising:

a display section that displays thereon tube individual data and a discharge program of the fluid;
an operation section for use to operate the control unit;
a control circuit section that drives and controls a motor; and
a tube individual data processing section that reads the tube individual data stored in the tube unit for data processing, wherein
the depression mechanism section has a rotation cam that sequentially deforms portions of the tube to transfer the fluid along a length of the tube,
the rotation cam sequentially depresses a plurality of depression members with respect to the tube from an inflow side to an outflow side thereof,
the rotation cam is configured by a first cam that is fixed to a center shaft and a second cam that is pivotally supported by the center shaft, and
the second cam is able to move from a position where the tube is free from the depression members to a position where the tube can be depressed thereby.

14. The control unit according to claim 13, further comprising
a transmission mechanism section that transfers rotation of the motor to the depression mechanism section.

* * * * *